US012577536B2

(12) United States Patent　　　　　(10) Patent No.:　US 12,577,536 B2
Osafune et al.　　　　　　　　　　　　(45) Date of Patent:　Mar. 17, 2026

(54) METHOD FOR ISOLATING URETERIC BUD TIP CELLS

(71) Applicant: KYOTO UNIVERSITY, Kyoto (JP)

(72) Inventors: Kenji Osafune, Kyoto (JP); Shinichi Mae, Kyoto (JP); Makoto Ryosaka, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 941 days.

(21) Appl. No.: 17/765,358

(22) PCT Filed: Sep. 30, 2020

(86) PCT No.: PCT/JP2020/037329
§ 371 (c)(1),
(2) Date: Mar. 30, 2022

(87) PCT Pub. No.: WO2021/066076
PCT Pub. Date: Apr. 8, 2021

(65) Prior Publication Data
US 2022/0380732 A1　　Dec. 1, 2022

(30) Foreign Application Priority Data
Oct. 1, 2019　(JP) ................................. 2019-181593

(51) Int. Cl.
*C12N 5/071*　　　(2010.01)
*G01N 33/569*　　(2006.01)

(52) U.S. Cl.
CPC ..... *C12N 5/0684* (2013.01); *G01N 33/56966* (2013.01); *C12N 2501/11* (2013.01); *C12N 2501/113* (2013.01); *C12N 2501/119* (2013.01); *C12N 2501/13* (2013.01); *C12N 2501/155* (2013.01); *C12N 2501/16* (2013.01); *C12N 2501/415* (2013.01); *C12N 2501/999* (2013.01); *C12N 2506/45* (2013.01)

(58) Field of Classification Search
CPC .......................... C12N 5/0684; C12N 2506/45
See application file for complete search history.

(56) References Cited

U.S. PATENT DOCUMENTS

| | | | |
|---|---|---|---|
| 2011/0008892 A1 | 1/2011 | Nigam et al. | |
| 2015/0284689 A1 | 10/2015 | Nigam | |
| 2019/0032020 A1 | 1/2019 | Takasato et al. | |

FOREIGN PATENT DOCUMENTS

| | | | |
|---|---|---|---|
| CN | 105473706 A | 4/2016 | |
| JP | 2006-312638 A | 11/2006 | |
| JP | 2017-537655 A | 12/2017 | |
| JP | 2018-183137 A | 11/2018 | |
| WO | WO 1997/018304 A1 | 5/1997 | |
| WO | WO 2013/186398 A1 | 12/2013 | |
| WO | WO 2014/066649 A1 | 5/2014 | |
| WO | WO 2014/197934 A1 | 12/2014 | |
| WO | WO 2019/098349 A1 | 5/2019 | |

OTHER PUBLICATIONS

Tsukahara et al., TROP2 Expressed in the Trunk of the Ureteric Duct Regulates Branching Morphogenesis during Kidney Development. PLoS One, published Dec. 14, 2011. (Year: 2011).*
Grote et al., Gata3 Acts Downstream of b-Catenin Signaling to Prevent Ectopic Metanephric Kidney Induction. PLoS Genetics. PLoS Genet 4(12), Dec. 2008. (Year: 2008).*
Bush et al., "TGF-β superfamily members modulate growth, branching, shaping, and patterning of the ureteric bud", Developmental Biology, 2004, 266(2): 285-298.
Chi et al., "A Secreted BMP Antagonist, Cer1, Fine Tunes the Spatial Organization of the Ureteric Bud Tree during Mouse Kidney Development", PLoS One, 2011, 6)(11): e27676.
Gui et al., "The loss of Trps1 suppresses ureteric bud branching because of the activation of TGF-β signa", Developmental Biology, 2013, 377: 415-427.
International Preliminary Report on Patentability for PCT International Patent Application No. PCT/JP2020/037329, dated Apr. 5, 2022.
International Search Report for PCT International Patent Application No. PCT/JP2020/037329, dated Dec. 8, 2020.
Kobayashi et al., "Six2 defines and regulates a multipotent self-renewing nephron progenitor population throughout mammalian kidney development", Cell Stem Cell, 2008, 3(2): 169-181.
Koehler et al., "Generation of inner ear organoids containing functional hair cells from human pluripotent stem cells", Nature Biotechnology, 2017, 35, 583-589.
Mae et al., "Expansion of Human iPSC-Derived Ureteric Bud Organoids with Repeated Branching Potential", Cell Reports, Jul. 1, 2020, 32(4): 107963.
Mae et al., "Generation of branching ureteric bud tissues from human pluripotent stem cells", Biochemical and Biophysical Research Communications, 2017, 495(1): 954-961.
Osafune et al., "Identification of multipotent progenitors in the embryonic mouse kidney by a novel colony-forming assay", Development, 2006, 133: 151-161.
Rutledge et al., "Cellular heterogeneity in the ureteric progenitor niche and distinct profiles of branching morphogenesis in organ development", Development, 2017, 144: 3177-3188.
Stewart et al., "Coordinated cell behaviours in early urogenital system morphogenesis", Semin Cell Dev Biol., 2017, 36: 13-20.

(Continued)

*Primary Examiner* — Laura Schuberg
*Assistant Examiner* — Nicholas A Humphries
(74) *Attorney, Agent, or Firm* — Lathrop GPM LLP; James H. Velema, Esq.; Judith Stone-Hulslander

(57) ABSTRACT

Provided is a method for isolating a ureteric bud tip cell from cells, a tissue, or an organoid comprising the ureteric bud tip cell, comprising the following steps of contacting the cells, tissue, or organoid comprising the ureteric bud tip cell with a very low density lipoprotein receptor (VLDL-R) binding agent, and isolating the ureteric bud tip cell using the binding agent as an indicator.

8 Claims, 16 Drawing Sheets

(56)     References Cited

OTHER PUBLICATIONS

Taguchi et al., "Redefining the in vivo origin of metanephric nephron progenitors enables generation of complex kidney structures from pluripotent stem cells", Cell Stem Cell, 2014, 14(1): 53-67.

Wang et al., "Dissecting the Global Dynamic Molecular Profiles of Human Fetal Kidney Development by Single-Cell RNA Sequencing", Cell Reports, 2018, 24: 3554-3567.

Yuri et al., "In Vitro Propagation and Branching Morphogenesis from Single Ureteric Bud Cells", Stem Cell Reports, 2017, 8(2): 401-416.

Extended European Search Report for corresponding European Patent Application No. 20872677.8, dated Oct. 23, 2023.

Taguchi et al., "Higher-Order kidney organogenesis from pluripotent stem cells", Elsevier, Cell Stem Cell, Epub Nov. 9, 2017, 21(6): 730-746.

Xia et al., "Directed differentiation of human pluripotent cells to ureteric bud kidney progenitor-like cells" Nature Cell Biology, 2013, 15(12): 1507-1515.

Bussolati et al., "Isolation of Renal Progenitor Cells from Adult Human Kidney", The American Journal of Pathology, Feb. 2005, 166(2): 545-555.

* cited by examiner

FIG. 1

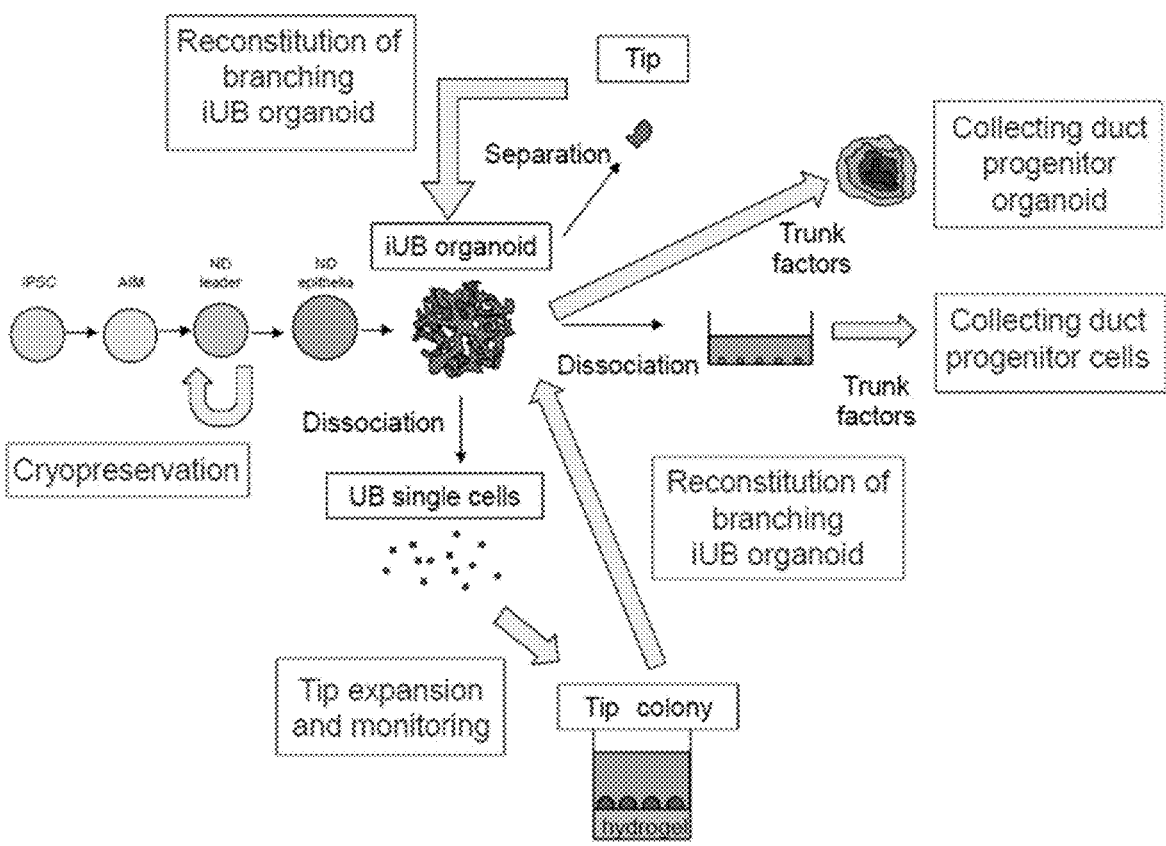

| Stage 1 | Stage 2 | Stage 3 | Stage 4 | Stage 5 | Stage 6 |
|---------|---------|---------|---------|---------|---------|
| APS | Anterior IM | | ND elongation | ND epithelialization | UB budding and branching |
| iMatrix-511 silk (2D) | Matrigel (2D) | | | Low attachment plate (3D) | 60% Matrigel (3D) |
| A C3 (B) | F8 TT A83 LDN | F8 TT A83 LDN Y | C1 LDN F8 G | G F1 TT C3 Tzv | G F1 TT C3 Tzv |
| 1 d | 2 d | 1 d | 2 d | 2 d | 15 d |

(b)

| Stage 1 | Stage 2 | Stage 3 | Stage 4 | Stage 5 | Stage 6 |
|---------|---------|---------|---------|---------|---------|
| APS | Anterior IM | | ND elongation | ND epithelialization | UB budding and branching |
| iMatrix-511 silk (2D) | Matrigel (2D) | | | Low attachment plate (3D) | 2% Matrigel (3D) |
| A C3 | F8 TT A83 LDN | F8 TT A83 LDN Y | C1 LDN F8 G TT | C1 LDN F8 G TT Y | C1 LDN F8 G TT F1 E |
| 1 d | 2 d | 1 d | 2 d | 2 d | 6 d |

E-CADHERIN   E-CADHERIN
GATA3 Nuclei   PAX2 Nuclei

Day 0     Day 2     Day 4

Matrigel (-)

Matrigel (+)

FIG. 10

Matrigel

RET CK8    LAMININ    LAMININ
Nuclei    EZRIN  Nuclei    PAX2  Nuclei

FIG. 13

EGF(-)
FGF1(-)

EGF(+)
FGF1(+)

RET
GATA3

FIG. 20
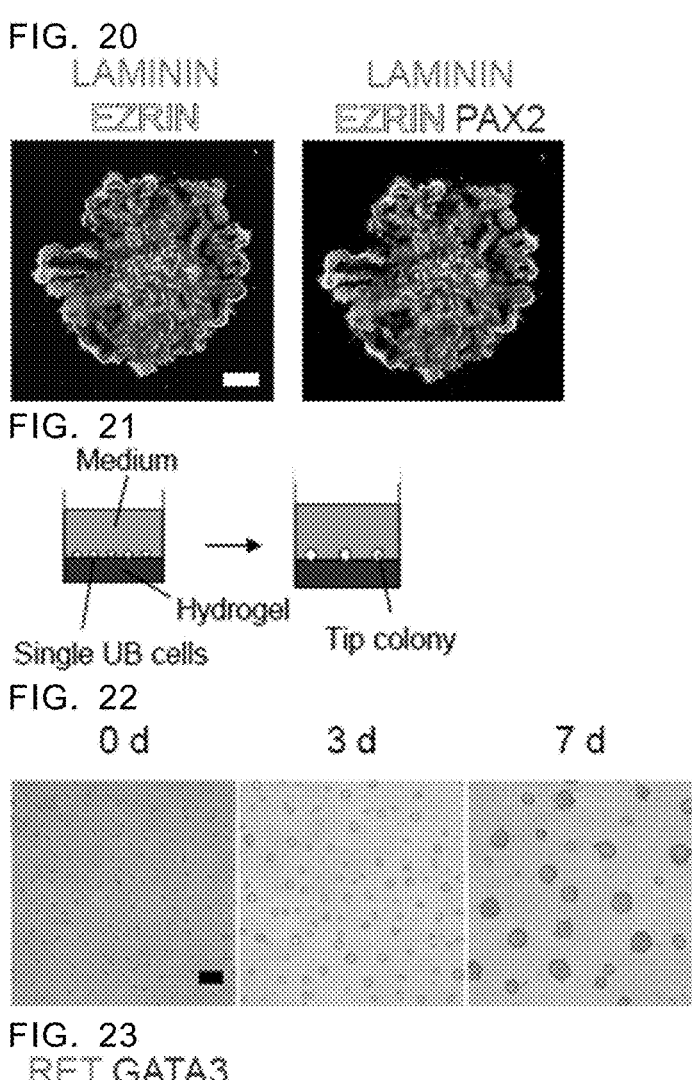
FIG. 21
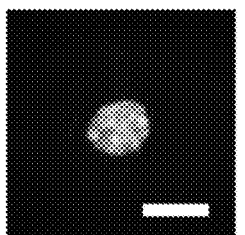
FIG. 22
0 d     3 d     7 d
FIG. 23
RET GATA3
FIG. 24
CK8     VLDLR     RET     Merge
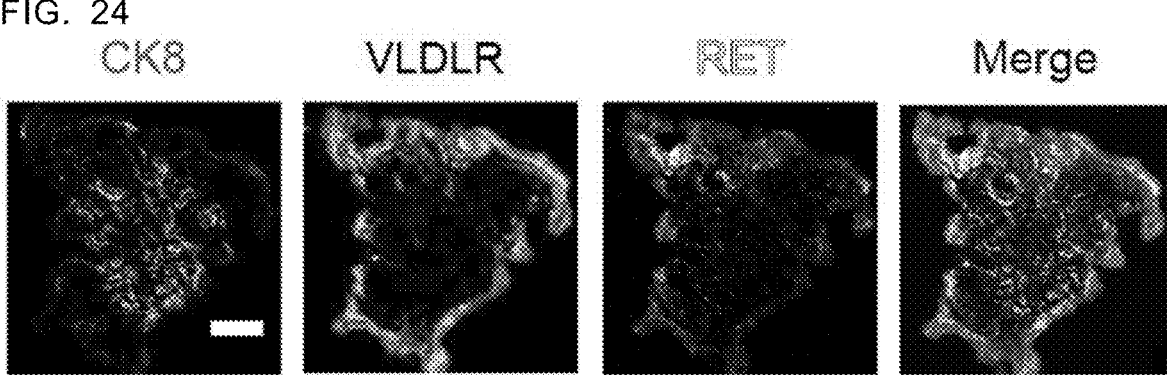

Tip colony

FIG. 32
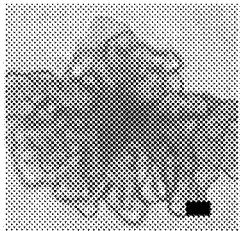
FIG. 33
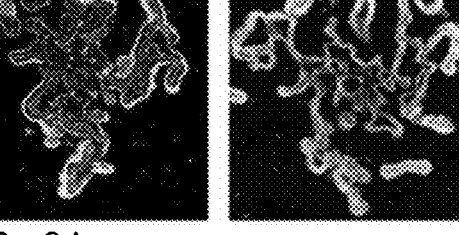
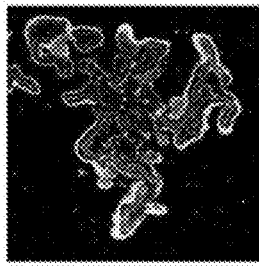
FIG. 34
0 d        7 d        14 d
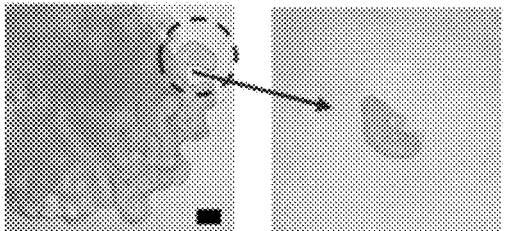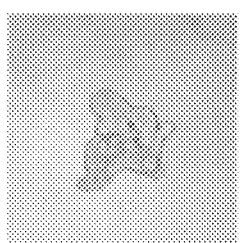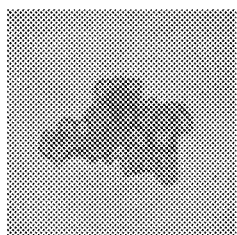
FIG. 35
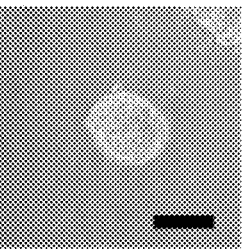
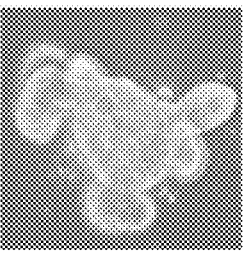

FIG. 40
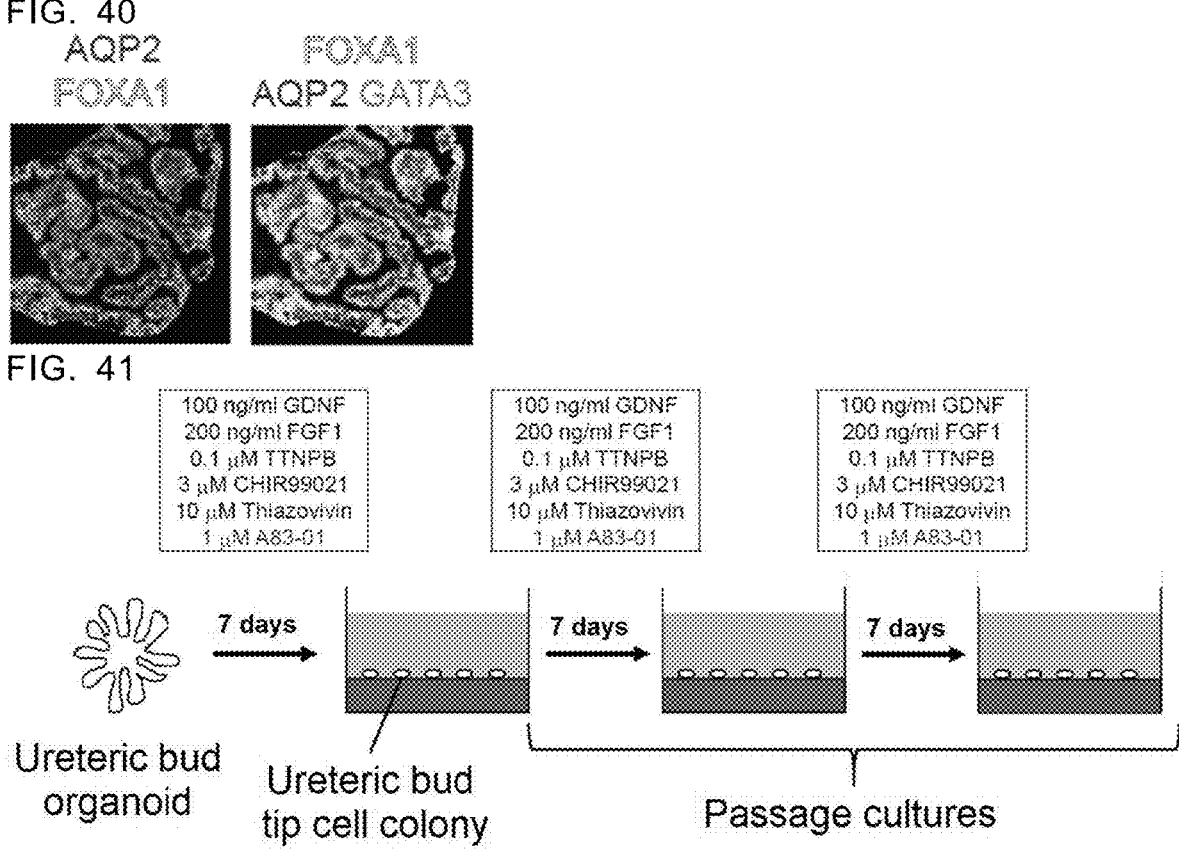
FIG. 41
100 ng/ml GDNF
200 ng/ml FGF1
0.1 μM TTNPB
3 μM CHIR99021
10 μM Thiazovivin
1 μM A83-01
100 ng/ml GDNF
200 ng/ml FGF1
0.1 μM TTNPB
3 μM CHIR99021
10 μM Thiazovivin
1 μM A83-01
100 ng/ml GDNF
200 ng/ml FGF1
0.1 μM TTNPB
3 μM CHIR99021
10 μM Thiazovivin
1 μM A83-01
7 days        7 days        7 days
Ureteric bud
organoid
Ureteric bud
tip cell colony
Passage cultures
FIG. 42
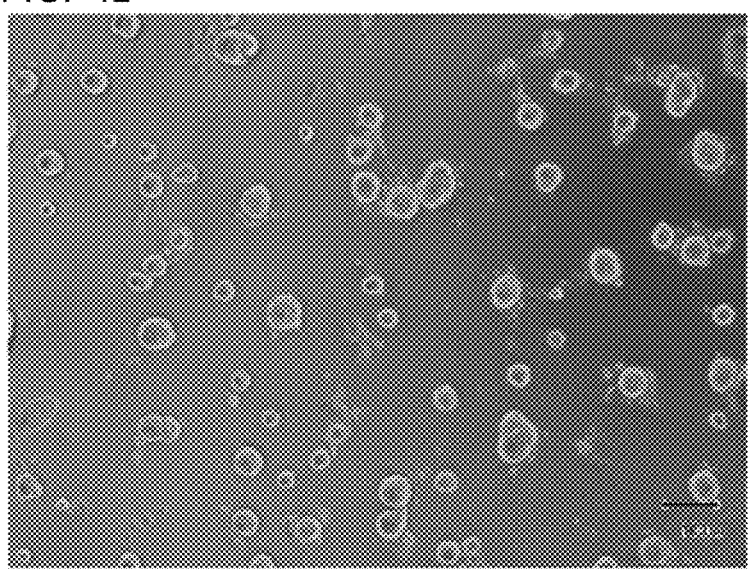

FIG. 43
GATA3 RET          GATA3 SOX9
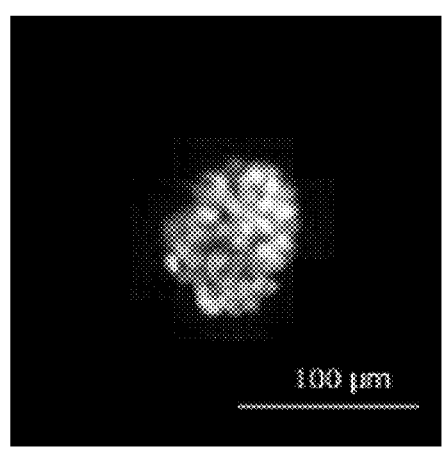 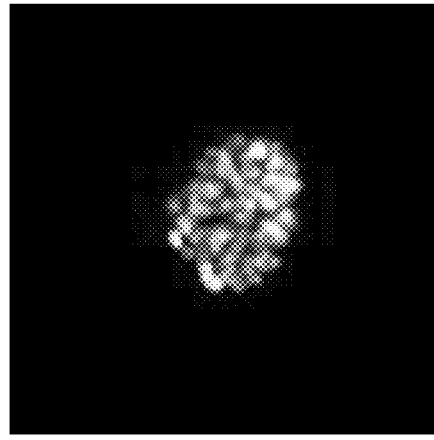
FIG. 44
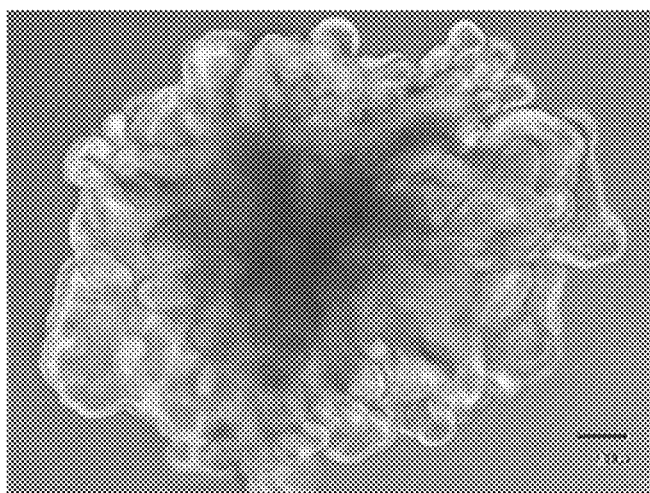
FIG. 45

FIG. 46
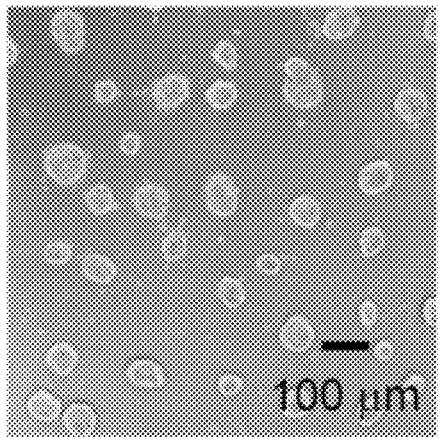
FIG. 47
GATA3 RET                    GATA3 SOX9
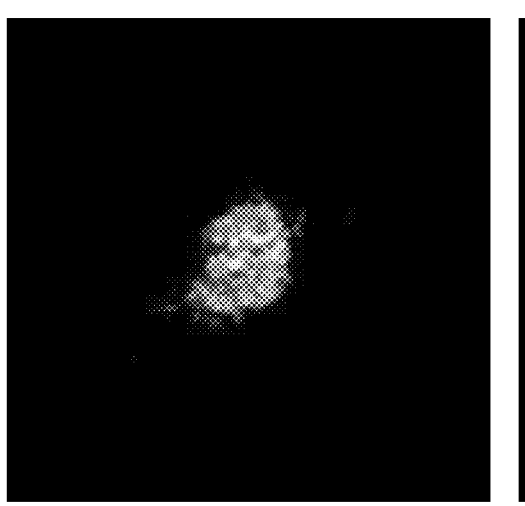   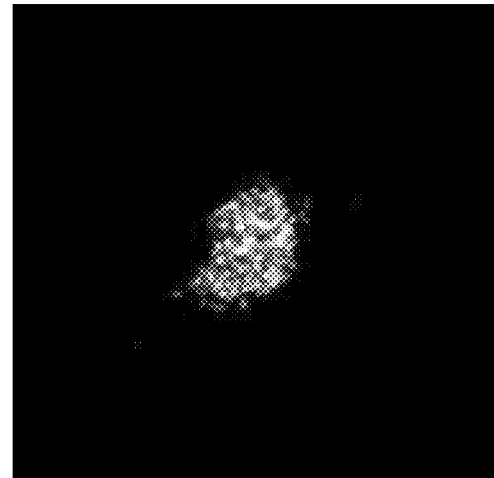
FIG. 48
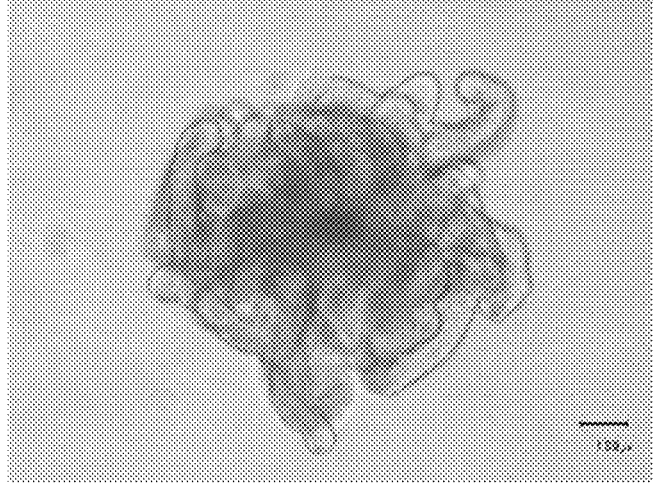

GATA3 RET

METHOD FOR ISOLATING URETERIC BUD TIP CELLS

TECHNICAL FIELD

This application claims the priority of Japanese Patent Application No. 2019-181593, the entire contents of which are incorporated herein by reference.

This application relates to a method for isolating a ureteric bud tip cell.

BACKGROUND

At present, the number of chronic kidney disease (CKD) patients in Japan is estimated to be about 13 million, and CKD is called as a new national disease. There are few curative treatments for chronic kidney disease. There are more than 330,000 end-stage chronic renal failure patients who require dialysis due to progression of the disease, which is a serious problem both medically and economically. Kidney transplantation is one of the curative treatments for chronic kidney disease including end-stage chronic renal failure, but its demand far exceeds its supply due to severe shortage of donor organs.

The kidney is derived from the intermediate mesoderm, which is an early embryonic tissue. For vertebrates, the intermediate mesoderm forms three kidney structures: pronephros, mesonephros and metanephros. For mammals, the metanephros forms the adult kidney. The metanephros is formed by the interaction between two tissues, the mesenchyme and the ureteric bud (non-patent literatures 1 and 2). In addition, it has been recently reported that the intermediate mesoderm is divided into two domains, the anterior and posterior, and the ureteric bud emerges from the anterior intermediate mesoderm and the mesenchyme emerges from the posterior intermediate mesoderm (non-patent literature 3).

The ureteric bud is an embryonic progenitor tissue that gives rise to the lower urinary tract, from the renal collecting duct to a part of the bladder. The ureteric bud is composed of tip and trunk. The tip is believed to serve as stem cells for ureteric bud that self-renew and provide daughter cells for tip cells and trunk cells.

If a method for efficiently producing ureteric bud cells/tissues derived from human iPS cells or human ES cells can be established, it is believed that the produced ureteric bud cells/tissues can be used as a source of lower urinary tract cells for a cell therapy. The produced ureteric bud cells/tissues can also be expected to solve the shortage of donors for kidney transplantation by contributing to the reconstruction of the three-dimensional kidney structures from human iPS cells or human ES cells in future. The produced ureteric bud cells/tissues can also be useful for creating renal disease models since many renal diseases occur in the ureteric bud, and the collecting duct and lower urinary tract derived from it. In addition, it can be expected to develop the research on the drug evaluation system for nephrotoxicity and therapeutic drug development using collecting duct cells, lower urinary tract cells, and kidney tissues containing them.

CITATION LIST

Patent Literature

[Patent Literature 1] WO2019/098349

Non-Patent Literature

[Non-Patent Literature 1] Osafune K., et al., Development 2006; 133:151-161.

[Non-Patent Literature 2] Kobayashi A., et al., Cell Stem Cell 2008; 3:169-181.

[Non-Patent Literature 3] Taguchi A., et al., Cell Stem Cell. 2014; 14:53-67.

SUMMARY OF INVENTION

Technical Problem

An object of the present application is to provide a method for isolating a ureteric bud tip cell from cells, a tissue, or an organoid comprising the ureteric bud tip cell.

Solution to Problem

The present application provides a method for isolating a ureteric bud tip cell from cells, a tissue, or an organoid comprising the ureteric bud tip cell, comprising the following steps of:

(1-1) contacting the cells, tissue, or organoid comprising the ureteric bud tip cell with a very low density lipoprotein receptor (VLDL-R) binding agent, and (1-2) isolating the ureteric bud tip cell using the binding agent as an indicator.

The present application also provides a method for producing a ureteric bud tip cell colony, comprising:

isolating a ureteric bud tip cell by the method of the present application, and the step of (2) culturing the ureteric bud tip cell in a medium comprising glial cell line-derived neurotrophic factor, a fibroblast growth factor, a retinoic acid receptor agonist, a GSK3$\beta$ inhibitor, and a Yes-associated protein (YAP) activity inhibitor.

The present application also provides a method for producing a ureteric bud-like organoid, comprising the following steps of:

providing a ureteric bud tip cell colony, and (3) culturing the ureteric bud tip cell colony in a medium comprising a Wnt signaling activator, a BMP inhibitor, a fibroblast growth factor, a retinoic acid receptor agonist, and glial cell line-derived neurotrophic factor to reconstitute the ureteric bud-like organoid.

The present application also provides a method for producing a collecting duct progenitor-like organoid, comprising the following steps of:

providing a ureteric bud-like organoid, and (4) culturing the ureteric bud-like organoid in a medium comprising a Wnt signal inhibitor and a TGF$\beta$ signal inhibitor.

The present application also provides a method for a producing collecting duct progenitor cell, comprising:

isolating a ureteric bud tip cell by the method of the present application, and the step of (2') culturing the ureteric bud tip cell in a medium comprising a Wnt signal inhibitor.

The present application also provides a method for producing a collecting duct progenitor cell, comprising:

obtaining a ureteric bud tip cell colony by the method of the present application, and the steps of (3'-1) dissociating the ureteric bud tip cell colony, and (3'-2) culturing the dissociated cell population in a medium comprising a Wnt signal inhibitor.

The present application also provides a method for producing a ureteric bud tip cell population, comprising the following steps of:

(1-1) contacting cells, a tissue, or an organoid comprising a ureteric bud tip cell with a VLDL-R binding agent, and (1-2) isolating the ureteric bud tip cell using the binding agent as an indicator.

The present application also provides a method for monitoring a ureteric bud tip cell, comprising the following steps of:

(i) contacting a biological tissue, a tissue fragment, cultured cells, or a cultured tissue predicted to comprise the ureteric bud tip cell with a VLDL-R binding agent, and (ii) detecting the binding agent.

The present application also provides a composition for isolating or monitoring a ureteric bud tip cell, comprising a VLDL-R binding agent.

Effects of the Invention

A ureteric bud tip cell can be efficiently isolated from cells, a tissue, or an organoid comprising the ureteric bud tip cell by the methods of the present application.

BRIEF DESCRIPTION OF DRAWINGS

FIG. 1 A schematic summarizing the methods established in the Examples. Cryopreservation of nephric duct leading edge cells (ND leader cells), isolation and expansion of ureteric bud (UB) tip cells, generation and reconstitution of branching induced ureteric (iUB) bud organoids, and induction of collecting duct progenitors have been achieved.

FIG. 2 The inventors' previous (a) and new (b) protocols of differentiation of hiPSCs/ESCs into ureteric bud (UB) cells through anterior primitive streak. APS: Anterior primitive streak; Anterior IM: Anterior intermediate mesoderm; ND: Nephric duct; UB: Ureteric bud. A: 100 ng/ml Activin A; C3: 3μ M CHIR99021; B: 10 ng/ml BMP4; F8: 200 ng/ml FGF8; TT: 0.1 μM TTNPB; A83: 1 μM A83-01; LDN: 0.1 μM LDN193189; Y: 10 μM Y-27632; C1: 1 μM CHIR99021; G: 100 ng/ml GDNF; F1: 200 ng/ml FGF1; E: 50 ng/ml EGF; Tzv: 10 μM Thiazovivin.

FIG. 10 Morphology of day 7 aggregates cultured with high (50%, left panel) and low (28, right panel) concentrations of Matrigel. Scale bar: 100 μm.

FIG. 11 Immunostaining analysis of a day 7 iUB organoid for PAX2 (green), EZRIN (red) and LAMININ (purple). Scale bar: 100 μm.

FIG. 12 Immunostaining analysis of a day 6 iUB organoid for RET (green) and CK8 (red; left panel), LAMININ (white) and EZRIN (red; middle panel), and LAMININ (white) and PAX2 (green; right panel). Scale bar: 100 μm.

FIG. 13 Morphology of tips separated from day 6 iUB organoids. Scale bar: 100 μm.

FIG. 14 Morphological changes of a tip organoid separated from a day 6 iUB organoid for the first 7 days. Scale bar: 100 μm.

FIG. 15 Immunostaining analysis of a day 14 separated tip organoid for PAX2 (blue), RET (green) and CK8 (red). Scale bar: 100 μm.

FIG. 16 3D whole mount immunostaining of a day 14 separated tip organoid for GATA3 (green), RET (white) and E-CADHERIN (red).

FIG. 20 Immunostaining analysis of a day 6 iUB organoid cultured in organoid medium containing EGF and FGF1 for LAMININ (green), EZRIN (white) and PAX2 (red). Scale bar: 100 μm.

FIG. 21 A schematic showing the formation of tip cell colonies from single cells derived from iUB organoids on hydrogel.

FIG. 22 Morphological changes of single cells dissociated from iUB organoids for 7 days. Scale bar: 100 μm.

FIG. 23 Immunostaining analysis of a day 7 tip cell colony for RET (green) and GATA3 (red). Scale bar: 100 μm.

FIG. 24 Immunostaining analysis of a day 7 iUB organoid for CK8 (green), VLDLR (red) and RET (white). Scale bar: 100 μm.

FIG. 32 Morphology of a day 18 iUB organoid derived from a tip cell colony and cultured in organoid medium containing low concentration Matrigel after hydrogel culture. Scale bar: 300 µm.

FIG. 33 Immunostaining analysis of a day 18 iUB organoid derived from a tip cell colony for EZRIN (green; left panel), LAMININ (red; left panel), GATA3 (red; right panel), and RET (green; right panel). Scale bar: 100 µm.

FIG. 34 Morphological changes of a tip separated from a day 14 iUB organoid for 14 days. Scale bar: 100 µm.

FIG. 35 Morphology of day 7 iUB organoids reconstituted from tip cell colonies cultured in organoid medium containing CHIR99021 or Wnt3a. Scale bar: 100 µm.

FIG. 40 Immunostaining analysis of a day 14 collecting duct progenitor organoid for FOXA1 (white), AQP2 (red), and GATA3 (green).

FIG. 41 A schematic showing the passage culture of tip cell colonies induced from iUB organoids.

FIG. 42 Morphology of tip cell colonies induced by dissociating iUB organoids into single cells and culturing them in the medium further containing A83-01. Scale bar: 100 µm.

FIG. 43 Immunostaining analysis of a tip cell colony induced in the medium further containing A83-01 for GATA3 (green), RET (red), and SOX9 (purple).

FIG. 44 Morphology of an iUB organoid derived from a tip cell colony induced in the medium further containing A83-01.

FIG. 45 Immunostaining analysis of an iUB organoid derived from a tip cell colony induced in the medium further containing A83-01 for GATA3 (green) and RET (red).

FIG. 46 Morphology of tip cell colonies after three passage cultures.

FIG. 47 Immunostaining analysis of a tip cell colony after three passage cultures for GATA3 (green), RET (red), and sox9 (purple).

FIG. 48 Morphology of an iUB organoid derived from a tip cell colony after three passage cultures.

DETAILED DESCRIPTION

Figures 3, 4, 5:
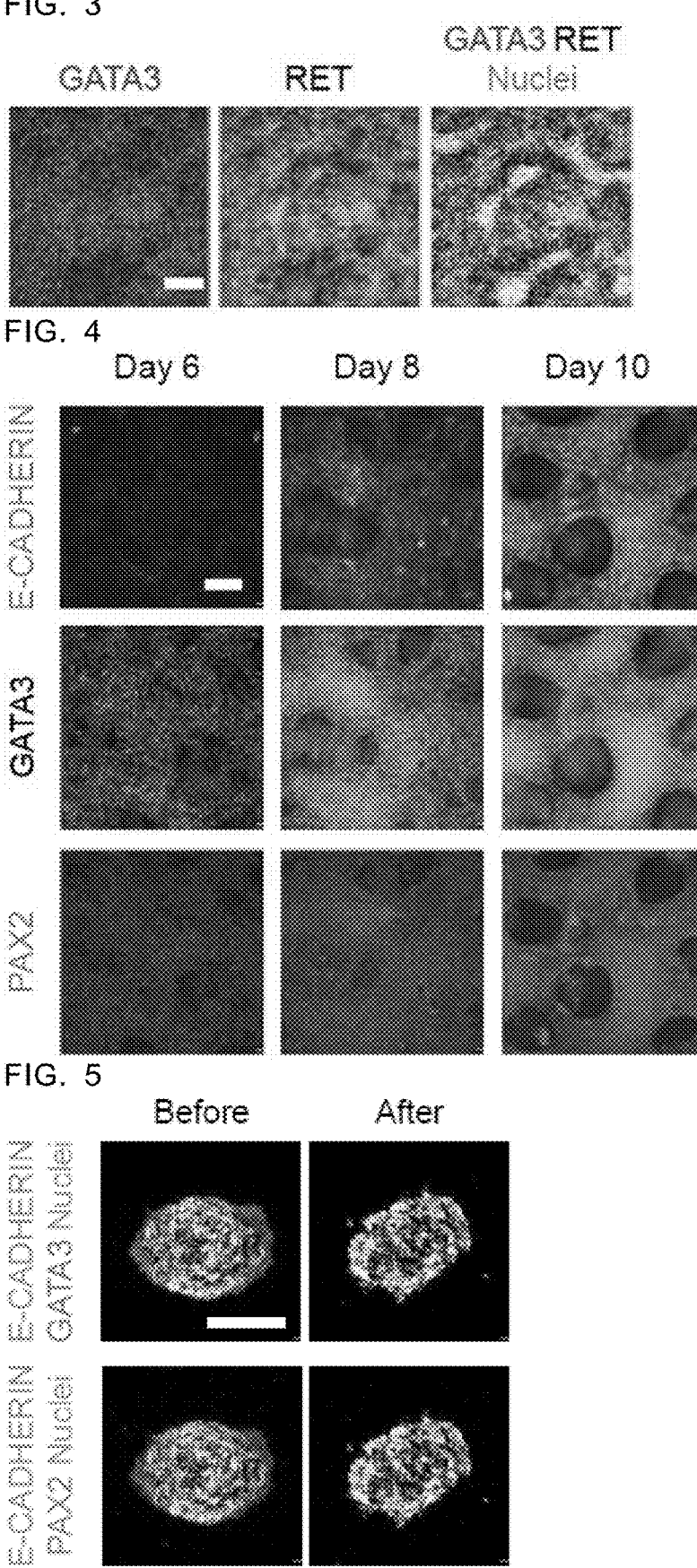
FIG. 3 Immunostaining analysis of Stage 4 day 2 cells for ND leader markers, GATA3 (green) and RET (red). Scale bar: 100 μm.
FIG. 4 Immunostaining analysis of Stage 4 day 6, 8 and 10 cells for E-CADHERIN (green), GATA3 (red) and PAX2 (purple) indicates that growth factors used at nephric duct (ND) elongation stage (Stage 4) enhance the epithelialization of ND leader cells. Scale bar: 100 μm.
FIG. 5 Immunostaining analysis of day 2 aggregates before and after removing non-ND cells for E-CADHERIN (green), GATA3 (red) and PAX2 (purple). Scale bar: 100 μm.

In this disclosure, when a numerical value is accompanied with the term "about", the value is intended to include the range of ±10% of that value. For example, "about 20" includes "18 to 22". A numerical range includes all values between the two endpoints and the values of both endpoints. When a numerical range is accompanied with "about", "about" is applied to the two endpoints. Accordingly, for example, "about 20 to 30" includes "18 to 33".

In the specification and claims of the present application, the expression "specific type of cells" means a cell group containing the type of cells unless otherwise specified, and the cell group may include cells other than the specified type of cells. For example, the expression "culture of a specific type of cells" means a culture of a cell group containing the type of cells, and may include cells other than the specified type of cells. Likewise, the expression "cell population of a specific type of cells" means cell population containing the type of cells unless otherwise specified, and the cell population may include cells other than the specified type of cells.

In the present application, a medium may be prepared by appropriately adding necessary factors to a basal medium for animal cell culture. Examples of basal media include MEM Zinc Option medium, IMEM Zinc Option medium, IMDM medium, Medium 199 medium, Eagle's Minimum Essential Medium (EMEM) medium, αMEM medium, Dulbecco's modified Eagle's Medium (DMEM) medium, DMEM/F12 medium, Ham's F12 medium, RPMI 1640 medium, Fischer's medium, and a mixed medium thereof. The basal medium may contain serum (e.g., fetal bovine serum (FBS)) or may be a serum-free medium. If necessary, the basal medium may comprise one or more serum substitutes, such as albumin, transferrin, KnockOut Serum Replacement (KSR) (Thermo Fisher Scientific) which is a serum substitute used for culturing an ES cell, N2 supplement (Thermo Fisher Scientific), B27 supplement (Thermo Fisher Scientific), a fatty acid, insulin, collagen precursor, a trace element, 2-mercaptethanol, and 3'-Thiolglycerol. In addition, the basal medium may comprise one or more substances, such as lipid, an amino acid, L-glutamine, GlutaMAX (Thermo Fisher Scientific), a nonessential amino acid (NEAA), a vitamin, a growth factor, an antibiotic, an antioxidant, pyruvic acid, a buffering agent, an inorganic salt, and equivalents thereof, and one or more other substances normally added to a medium for animal cell culture.

The basal medium used in the present application may be, for example, DMEM/F12 medium or Essential 6™ medium (Thermo Fisher Scientific) which is serum-free DMEM/F12 medium supplemented with L-ascorbic acid-2-phosphate magnesium, sodium selenium, insulin, NaHCO₃ and transferrin.

In the specification and claims of the present application, "isolation" means that components of interest (e.g., cells, tissues, and organoids) are out of the original state by removing components other than the components of interest. In the present application, the isolation or production of cells, tissues or organoids of interest can be confirmed by the expression of their markers, their size, and/or their shape. The expression of the markers can be confirmed by known methods, such as immunostaining, flow cytometry, FACS (fluorescence-activated cell sorting), and MACS (magnetic-activated cell sorting).

Method for Isolating a Ureteric Bud Tip Cell from Cells, a Tissue, or an Organoid Comprising the Ureteric Bud Tip Cell In one aspect of the present application, provided is a method for isolating a ureteric bud tip cell from cells, a tissue, or an organoid comprising the ureteric bud tip cell, comprising the following steps of:

(1-1) contacting the cells, tissue, or organoid comprising the ureteric bud tip cell with a very low density lipoprotein receptor (VLDL-R) binding agent, and (1-2) isolating the ureteric bud tip cell using the binding agent as an indicator.

"Ureteric bud tip cell" means a cell at the tip of a budding or branching region of a ureteric bud tissue or a ureteric bud-like organoid. A ureteric bud tip cell can be confirmed by the expression of RET or very low density lipoprotein receptor (VLDL-R), or the uptake of very low density lipoprotein (VLDL). Cells, a tissue, or an organoid comprising a ureteric bud tip cell may be of mammalian origin, for example primate origin, preferably human origin.

In one embodiment, the cells, tissue, or organoid comprising the ureteric bud tip cell is a ureteric bud-like organoid. "Ureteric bud-like organoid" means a ureteric bud-like self-organized structure having branching structure. The size of a ureteric bud-like organoid is, for example, about 10 to about 1000 μm. A ureteric bud-like organoid branches, for example, 3 to 5 times. A ureteric bud-like organoid can be confirmed by the expression of the markers, such as GATA3, RET, PAX2 and CALB1. The branching structure of a ureteric bud-like organoid can be confirmed under a microscope.

The ureteric bud-like organoid may be induced from a pluripotent stem cell. A method for inducing a ureteric bud-like organoid from a pluripotent stem cell is known, and any known method may be used. For example, the method described in WO2019/098349 can be used.

In the present application, "pluripotent stem cell" refers to a stem cell which has pluripotency, which is the ability to differentiate into all cell types in a living body, as well as proliferative capacity. Examples of the pluripotent stem cells include embryonic stem (ES) cells (J. A. Thomson et al., (1998), Science 282:1145-1147; J. A. Thomson et al., (1995), Proc. Natl. Acad. Sci. USA, 92:7844-7848; J. A. Thomson et al., (1996), Biol. Reprod., 55:254-259; J. A. Thomson and V. S. Marshall (1998), Curr. Top. Dev. Biol., 38:133-165), embryonic stem cells derived from cloned embryos obtained by nuclear transfer (ntES cells) (T. Wakayama et al., (2001), Science, 292:740-743; S. Wakayama et al., (2005), Biol. Reprod., 72:932-936; J. Byrne et al., (2007), Nature, 450:497-502), germline stem cells ("GS cells") (M. Kanatsu-Shinohara et al., (2003) Biol. Reprod., 69:612-616; K. Shinohara et al., (2004), Cell, 119:1001-1012), embryonic germ cells ("EG cells") (Y. Matsui et al., (1992), Cell, 70:841-847; J. L. Resnick et al., (1992), Nature, 359:550-551), induced pluripotent stem (iPS) cells (K. Takahashi and S. Yamanaka (2006) Cell, 126:663-676; K. Takahashi et al., (2007), Cell, 131:861-872; J. Yu et al., (2007), Science, 318:1917-1920; Nakagawa, M. et al., Nat. Biotechnol. 26:101-106 (2008); WO 2007/069666), and pluripotent cells derived from cultured fibroblasts or bone marrow stem cells (Muse cells) (WO 2011/007900). In the present application, a pluripotent stem cell may be of mammalian origin, for example primate origin, preferably human origin. The pluripotent stem cell may also be, for example, an ES cell or an iPS cell.

iPS cells can be produced by introducing a specific reprogramming factor in the form of DNA or protein into somatic cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al, Nat. Biotechnol. 26:101-106 (2008); WO2007/069666). When iPS cells are used, the iPS cells may be produced from somatic cells by a known method, or may be those that have already been established and stocked. The somatic cells from which the iPS cells used in the present invention are derived are not limited, and, for example, can be peripheral blood-derived cells or cord blood-derived cells. The animal from which the pluripotent stem cells are derived is not limited, and examples thereof include mammals, such as mice, rats, hamsters, guinea pigs, cattle, horses, pigs, sheep, monkeys, orangutans, chimpanzees, dogs, cats, birds, and humans, preferably primates, and more preferably humans.

In step (1-1), the cells, tissue, or organoid comprising the ureteric bud tip cell is contacted with a very low density lipoprotein receptor (VLDL-R) binding agent.

In the present application, "very low density lipoprotein receptor (VLDL-R) binding agent" is not particularly limited as long as it is an agent having the property of binding to VLDL-R. Examples of VLDL-R binding agents include, but are not limited to, compounds, peptides, and proteins that have the property of binding to VLDL-R. For example, proteins that bind to VLDL-R may include ligands for VLDL-R, antibodies and antibody fragments having VLDL-R binding activity, and proteins comprising a VLDL-R binding domain. In one embodiment, the VLDL-R binding agent is "very low density lipoprotein (VLDL)". "Very low density lipoprotein (VLDL)" is one of the plasma lipoproteins classified by ultracentrifugation or electrophoresis. As used herein, VLDL can also include variants and modifications of VLDL that have VLDL-R binding activity. In step (1-1), the VLDL-R binding agent is typically added to the culture medium of the cells, tissue or organoid comprising the ureteric bud tip cell.

In one embodiment, the VLDL-R binding agent used in the present invention can be a labeled VLDL-R binding agent, e.g., labeled VLDL. The labeled VLDL-R binding agent or VLDL means a VLDL-R binding agent or VLDL that is bound to a label. The label can be a label known to those skilled in the art, such as a fluorescent label, a magnetic label, an enzyme, a coenzyme, a chemiluminescent label, a bioluminescent label, a radioactive label, and a metal. In the present application, the label is, for example, a fluorescent or label a magnetic label. Examples of fluorescent labels include Carbocyanine dyes (e.g., DiI, DiO, DiD, and DiR), fluorescein derivatives (e.g., fluorescein isothiocyanate (FITC), and fluorescein thioflubamyl), rhodamine derivatives (e.g., tetramethylrhodamine, trimethylrhodamine (RITC), Texas red, rhodamine 110), Cy Dyes (Cy3, Cy5, Cy5.5, Cy7), Cy-Chrome, Spectrum Green, Spectrum Orange, propidium iodide, allophycocyanine (APC), R-phycoerythrin (R-PE), and Alexa Fluor dyes. Commercially available labeled VLDL, for example, DiI-conjugated VLDL (DiI-VLDL; Biomedical Technologies, Inc.), can be used. Examples of magnetic labels include magnetic microbeads. The amount of a VLDL-R binding agent to be added is not particularly limited as long as it is detectable as an indicator. When DiI-VLDL is used, its concentration may be 10 ng/ml to 1 mg/ml, 100 ng/ml to 1 mg/ml, or 1 μg/ml to 100 μg/ml, and for example about 10 μg/ml.

In step (1-2), the ureteric bud tip cell is isolated using the binding agent as an indicator. For example, the binding agent may be labeled as described above, and the label may be used as an indicator. Alternatively, a labeled antibody that recognizes the binding agent may be added and the label may be used as an indicator. As a means for isolating a ureteric bud tip cell using the label as an indicator, a known method may be appropriately used depending on the type of label. For example, when the label is a fluorescent label, the cells can be isolated by flow cytometry or FACS (fluorescence-activated cell sorting). When the label is a magnetic label, the cells can be isolated by MACS (Magnetic-activated cell sorting).

Method for Producing a Ureteric Bud Tip Cell Population from Cells, a Tissue, or an Organoid Comprising Ureteric Bud Tip Cell

In one aspect of the present application, provided is a method for producing a ureteric bud tip cell population, comprising the following steps of:

(1-1) contacting cells, a tissue, or an organoid comprising a ureteric bud tip cell with a VLDL-R binding agent, and (1-2) isolating the ureteric bud tip cell using the binding agent as an indicator.

The steps (1-1) and (1-2) may be performed in the same manner as the steps (1-1) and (1-2) in the above method for isolating a ureteric bud tip cell from cells, a tissue, or an organoid comprising the ureteric bud tip cell.

Method for Producing a Ureteric Bud Tip Cell Colony from an Isolated Ureteric Bud Tip Cell

In one aspect of the present application, provided is a method for producing a ureteric bud tip cell colony, comprising:

isolating a ureteric bud tip cell by the method of the present application, and the step of (2) culturing the ureteric bud tip cell in a medium comprising glial cell line-derived neurotrophic factor, a fibroblast growth factor, a retinoic acid receptor agonist, a GSK3β inhibitor, and a Yes-associated protein (YAP) activity inhibitor.

A ureteric bud tip cell colony means a cell population grown from a single ureteric bud tip cell. The size of the ureteric bud tip cell colony is not particularly limited and can be appropriately determined by those skilled in the art according to the intended use. A ureteric bud tip cell colony can be confirmed by the expression of RET, GATA3, very low density lipoprotein receptor (VLDLR), or the uptake of very low density lipoprotein (VLDL).

In step (2), the ureteric bud tip cell isolated by the method of the present application may be seeded and cultured under a three-dimensional culture condition on the hydrogel obtained by diluting a three-dimensional scaffold material with the medium.

Various three-dimensional scaffold materials for constructing a three-dimensional structure of cultured cells are known and commercially available. The three-dimensional scaffold material is not particularly limited. For example, a collagen-based material, a polymer-based material, such as polycaprolactone and polyglycolic acid, or a complex thereof can be used. The form of the three-dimensional scaffold material is also not particularly limited, and examples thereof include a sponge-like structure. Further, the three-dimensional scaffold material may be a material derived from a living body, such as extracellular matrix and basement membrane. Specifically, the three-dimensional scaffold material can include Matrigel™ (Becton Dickinson and Company), type I collagen gel and type IV collagen gel. Matrigel™ basement membrane matrix is a soluble basement membrane preparation extracted from Engelbreth-Holm-Swarm (EHS) mouse sarcoma, which is rich in extracellular matrix proteins, and is composed primarily of laminin, collagen IV, entactin, and heparan sulfate proteoglycan. In addition, it may include other growth factors, such as TGF-β, a fibroblast growth factor, tissue plasminogen activator, and EHS.

In step (2), when Matrigel™ is used as the three-dimensional scaffold material, its concentration in the hydrogel may be 20% to 80%, 30% to 70%, or 40% to 60%, and for example about 50%.

In step (2), the concentration of glial cell line-derived neurotrophic factor may be 100 µg/ml to 10 µg/ml, 1 ng/ml to 10 µg/ml, or 10 ng/ml to 1 µg/ml, and for example about 100 ng/ml.

FGF1 to FGF23 are known as "fibroblast growth factors". The fibroblast growth factor may be appropriately selected from them. In step (2), the concentration of the fibroblast growth factor can be appropriately selected by those skilled in the art, depending on the fibroblast growth factor to be used. When the fibroblast growth factor is FGF1, its concentration may be 200 µg/ml to 20 µg/ml, 2 ng/ml to 20 µg/ml, or 20 ng/ml to 2 µg/ml, and for example about 200 ng/ml.

"Retinoic acid receptor (RAR) agonist" may be a naturally-occurring retinoid, a chemically synthesized retinoid, a retinoic acid receptor agonist compound not having the retinoid structure, or a natural substance having the retinoic acid receptor agonist activity. Examples of a natural retinoid having the RAR agonist activity include retinoic acid, such as known stereoisomers, all-trans retinoic acid (all-trans RA) and 9-cis retinoic acid (9-cis RA). A chemically synthesized retinoid is known to the art (e.g., U.S. Pat. Nos. 5,234,926 and 4,326,055). Examples of retinoic acid receptor agonist compounds not having the retinoid structure include Am80, AM580 (4-[[5,6,7,8-tetrahydro-5, 5, 8, 8-tetramethyl-2-naphthalenyl]carboxyamide]benzoic acid), TTNPB (4-[[E]-2-[5, 6, 7, 8-tetrahydro-5, 5, 8, 8-tetramethyl-2-naphthalenyl]-1-propenyl]benzoic acid), and AC55649 (4'-octyl-[1,1'-biphenyl]-4-carboxylic acid). Examples of natural substances having the retinoic acid receptor agonist activity include honokiol and magnolol (Annual Report of Research Institute for Biological Function 9:55-61, 2009). The RAR agonist used in the present application may be retinoic acid, AM580, TTNPB, and AC55649, and for example TTNPB. In step (2), the concentration of the retinoic acid receptor agonist can be appropriately selected by those skilled in the art, depending on the retinoic acid receptor agonist to be used. When the retinoic acid receptor agonist is TTNPB, its concentration may be 0.1 nM to 10 µM, 1 nM to 10 µM, or 10 nM to 1 µM, and for example about 0.1 µM.

"GSK3β inhibitor" is defined as a substance which inhibits the kinase activity of a GSK3β protein, such as an ability to phosphorylate β-catenin, and many GSK3β inhibitors are known. Examples of the GSK3β inhibitors include BIO (also called GSK3β inhibitor IX; 6-bromoindirubin3'-oxime) which is a derivative of indirubin, SB216763 (3-(2, 4-dichlorophenyl)-4-(1-methyl-1H-indol-3-yl)-1H-pyrrole-2, 5-dione) and SB415286 (3-[(3-chloro-4-hydroxyphenyl)amino]-4-(2-nitrophenyl)-1H-pyrrole-2, 5-dione) which are derivatives of maleimide, GSK3β inhibitor VII (4-dibromoacetophenone) which is a phenyl α bromomethylketone compound, L803-mts (also called, GSK3β peptide inhibitor; Myr-N-GKEAPPAPPQSpP-NH2) which is a cell-penetrating phosphorylated peptide, and CHIR99021 (6-[2-[4-(2, 4-Dichlorophenyl)-5-(4-methyl-1H-imidazole-2-yl)pyrimidine-2-ylamino]ethylamino]pyridine-3-carbonitrile) which has high selectivity. These compounds are commercially and easily available, for example, from Calbiochem and Biomol. The GSK3β inhibitor used in the present application may be, for example, CHIR99021. In step (2), the concentration of the GSK3β inhibitor can be appropriately selected by those skilled in the art, depending on the GSK3β inhibitor to be used. When the GSK3β inhibitor is CHIR99021, its concentration may be 3 nM to 300 µM, 30 nM to 300 µM, or 300 nM to 30 µM, and for example about 3 µM.

In step (2), the concentration of the YAP activity inhibitor can be appropriately selected by those skilled in the art, depending on the YAP activity inhibitor to be used. A known YAP activity inhibitor may be appropriately used. Examples of YAP activity inhibitors include Thiazovivin, which has both YAP inhibitory activity and ROCK inhibitory activity. When the YAP activity inhibitor is Thiazovivin, its concentration may be 10 nM to 1 mM, 100 nM to 1 mM, or 1 μM to 100 μM, and for example about 10 μM.

In step (2), the medium may further comprise a TGFβ signal inhibitor. "TGFβ signal inhibitor" is a substance which inhibits the signal transduction starting from the binding of TGFβ to its receptor and leading to SMAD. The TGFβ signal inhibitor is not particularly limited as long as it inhibits the binding of TGFβ to its receptor, an ALK family, or inhibits the phosphorylation of SMAD caused by the ALK family. Examples of TGEβ signal inhibitors include Lefty-1 (e.g., NCBI Accession Nos: NM_010094 (mouse), and NM_020997 (human)), SB431542 and SB202190 (R. K. Lindemann et al., Mol. Cancer, 2003, 2:20), SB505124 (GlaxoSmithKline), NPC30345, SD093, SD908, SD208 (Scios), LY2109761, LY364947, LY580276 (Lilly Research Laboratories), A83-01 (3-(6-Methyl-2-pyridinyl)-N-phenyl-4-(4-quinolinyl)-1H-pyrazole-1-carbo-thioamide, WO2009/146408), ALK5 inhibitor II (2-[3-[6-methylpyridine-2-yl]-1H-pyrazole-4-yl]-1,5-naphthyridine), TGEβRI kinase inhibitor VIII (6-[2-tert-butyl-5-[6-methyl-pyridine-2-yl]-1H-imidazole-4-yl]-qui-noxaline), and derivatives thereof. The TGFβ signal inhibitor used in the present application may be, for example, A83-01. In step (2), the concentration of the TGEβ signal inhibitor can be appropriately selected by those skilled in the art, depending on the TGFβ signal inhibitor to be used. When the TGFβ signal inhibitor is A83-01, its concentration may be 1 nM to 100 μM, 10 nM to 100 μM, or 100 nM to 10 μM, and for example about 1 μM.

In step (2), the culture period may be 2 to 21 days, 3 to 14 days, or 5 to 10 days, and for example about 6 to about 7 days.

A ureteric bud tip cell colony can be maintained by passaging it every 1 to 12 days, every 5 to 10 days, every 6 to 8 days, or every about 7 days. A ureteric bud tip cell colony can also be maintained by passaging it when it grows to its size of about 10 to about 1000 μm, about 15 to about 500 μm, about 20 to about 150 μm, or about 80 to about 100 μm. The number of passages is not particularly limited, and it can be passaged as many times as desired. For example, a ureteric bud tip cell colony can be passaged once, twice, three times, four times, five times, or more. The period of passage is not particularly limited, and it can be passaged for a desired period. For example, a ureteric bud tip cell colony can be passaged for 1 day or more, 7 days or more, 14 days or more, 21 days or more, 28 days or more, and for example 70 days or more.

The culture temperature is, but not limited to, about 30 to about 40° C., for example about 37° C. The culture may be performed in $CO_2$-containing air atmosphere. The $CO_2$ concentration is, for example, about 2 to about 5%.

Accordingly, the present invention also provides a method for passaging a ureteric bud tip cell colony. The substances added to the medium for passage culture and their concentrations are as described above. As an example, glial cell line-derived neurotrophic factor (e.g., about 100 ng/ml GDNF), a fibroblast growth factor (e.g., about 200 ng/ml FGF1), a retinoic acid receptor agonist (e.g., about 0.1 μM TTNPB), a GSK3β inhibitor (e.g., about 3 μM CHIR99021), a YAP activity inhibitor (e.g., about 10 μM Thiazovivin), and a TGFβ signal inhibitor (e.g., about 1 μM A83-01) are added to the medium. Other culture conditions are also as described above.

Method for Reconstituting a Ureteric Bud-Like Organoid from a Ureteric Bud Tip Cell Colony In one aspect of the present application, provided is a method for producing a ureteric bud-like organoid, comprising the following step of:

(3) culturing a ureteric bud tip cell colony in a medium comprising a Wnt signaling activator, a BMP inhibitor, a fibroblast growth factor, a retinoic acid receptor agonist, and glial cell line-derived neurotrophic factor to reconstitute the ureteric bud-like organoid. The ureteric bud tip cell colony may be obtained by the method of the present application or other known methods. In this step, the size of the ureteric bud tip cell colony may be, but not particularly limited to, for example about 10 to about 1000 μm.

In step (3), the ureteric bud tip cell colony is cultured in a medium comprising a Wnt signaling activator, a BMP inhibitor, a fibroblast growth factor, a retinoic acid receptor agonist, and glial cell line-derived neurotrophic factor. In one embodiment, in step (3), the ureteric bud tip cell colony is cultured under a suspension culture condition. In the present application, "suspension culture" refers to cell culture in the manner that the cells are not adhered to the culture plate. The culture plate to be used for suspension culture may be, but not particularly limited to, those having no artificial treatment that improves the cell adherence to the plate, such as culture plates having no extracellular matrix coatings, or those having artificial treatment to prevent cell adherence, such as culture plates having coating treatment with polyhydroxyethyl methacrylic acid (poly-HEMA) or 2-Methacryloyloxyethyl phosphorylcholine polymer (Lipi-dure). For example, commercially available products, such as low-attachment 35 mm dish (Sumitomo Bakelite), may be used.

In step (3), the concentration of the Wnt signaling activator can be appropriately selected by those skilled in the art, depending on the Wnt signaling activator to be used. The Wnt signaling activator used in the present application may be, for example, LiCl, Wnt1, Wnt3a, Wnt7a, or R-spondin 1. When the Wnt signaling activator is Wnt3a, its concentration may be about 5 to about 20%. Commercially available products, such as Afamin/Wnt3a conditioned medium, may be used. When the Wnt signaling activator is R-spondin 1, its concentration may be 200 pg/ml to 20 μg/ml, 2 ng/ml to 20 μg/ml, or 20 ng/ml to 2 μg/ml, and for example about 200 ng/ml.

Examples of "BMP inhibitors" include proteinous inhibitors, such as Chordin, Noggin and Follistatin, Dorsomorphin 6-[4-(2-piperidin-1-yl-ethoxy)phenyl]-3-pyridin-4-yl-pyra-zolo[1,5-a]pyrimidine and derivatives thereof (P. B. Yu et al. (2007), Circulation, 116: II_60; P. B. Yu et al. (2008), Nat. Chem. Biol., 4:33-41; J. Hao et al. (2008), PLOS ONE, 3 (8): e2904), and LDN193189 (4-(6-(4-(piperazin-1-yl)phe-nyl)pyrazolo[1,5-a]pyrimidin-3-yl)quinoline). The BMP inhibitor used in the present application may be, for example, LDN193189. In step (3), the concentration of the BMP inhibitor can be appropriately selected by those skilled in the art, depending on the BMP inhibitor to be used. When the BMP inhibitor is LDN193189, its concentration may be 0.1 nM to 10 μM, 1 nM to 10 μM, or 10 nM to 1 μM, and for example about 0.1 μM.

In step (3), the concentration of the fibroblast growth factor can be appropriately selected by those skilled in the art, depending on the fibroblast growth factor to be used. When the fibroblast growth factor is FGF8, its concentration may be 200 pg/ml to 20 μg/ml, 2 ng/ml to 20 μg/ml, or 20 ng/ml to 2 μg/ml, and for example about 200 ng/ml.

In step (3), the concentration of the retinoic acid receptor agonist can be appropriately selected by those skilled in the art, depending on the retinoic acid receptor agonist to be used. When the retinoic acid receptor agonist is TTNPB, its concentration may be 0.1 nM to 10 μM, 1 nM to 10 μM, or 10 nM to 1 μM, and for example about 0.1 μM.

In step (3), the concentration of glial cell line-derived neurotrophic factor may be 100 μg/ml to 10 μg/ml, 1 ng/ml to 10 μg/ml, or 10 ng/ml to 1 μg/ml, and for example about 100 ng/ml.

In step (3), the medium may further comprise EGF and/or FGF1. EGF is a protein called Epidermal Growth Factor. Commercially available EGF from R&D systems may be used. The concentration of EGF may be 50 pg/ml to 5 pg/ml, 500 pg/ml to 5 μg/ml, or 5 ng/ml to 500 ng/ml, and for example about 50 ng/ml. The concentration of FGF1 may be 200 pg/ml to 20 μg/ml, 2 ng/ml to 20 μg/ml, or 20 ng/ml to 2 μg/ml, and for example about 200 ng/ml.

In step (3), the medium may further comprise Matrigel. The concentration of Matrigel may be 1 to 40%, 2 to 30%, or 5 to 20%, and for example about 10%.

In step (3), the culture period may be 2 to 30 days, 5 to 20 days, or 8 to 15 days, and for example about 10 days.

The culture temperature is, but not limited to, about 30 to about 40° C., for example about 37° C. The culture may be performed in $CO_2$-containing air atmosphere. The $CO_2$ concentration is, for example, about 2 to about 5%.

Method for Producing a Collecting Duct Progenitor-Like Organoid from a Ureteric Bud-Like Organoid In one aspect of the present application, provided is a method for producing a collecting duct progenitor-like organoid, comprising the following step of:

(4) culturing a ureteric bud-like organoid in a medium comprising a Wnt signal inhibitor and a TGFβ signal inhibitor. The ureteric bud-like organoid to be used may be produced or reconstituted by the method of the present application or obtained by other known methods.

"Collecting duct progenitor-like organoid" means a collecting duct progenitor-like self-organized structure. The size of a collecting duct progenitor-like organoid is, for example, about 10 to about 1000 μm. A collecting duct progenitor-like organoid can be confirmed by the expression of the markers, such as AQP2.

In step (4), the ureteric bud-like organoid is cultured in a medium comprising a Wnt signal inhibitor and a TGFβ signal inhibitor. In one embodiment, in step (4), the ureteric bud-like organoid is cultured under a suspension culture condition.

"Wnt signal inhibitor" is not particularly limited as long as it inhibits a signaling pathway via Wnt. Examples of Wnt signal inhibitors include IWR-1, IWP-2, IWP-3, IWP-4, 2-(4-trifluoromethylphenyl)-7, 8-dihydro-5H-thiopyrano[4, 3-d]pyrimidin-4 (3H)-one (XAV939), G-CSF, IGFBP4, Dkk1, Cerberus, anti-Wnt antibody, Wnt antagonist (Wnt receptor inhibitor), soluble Wnt receptor proteins, such as Frzb-1, and dominant negative form. The Wnt signal inhibitor used in the present application may be, for example, IWR-1. In step (4), the concentration of the Wnt signal be inhibitor can appropriately selected by those skilled in the art, depending on the Wnt signal inhibitor to be used. When the Wnt signal inhibitor is IWR-1, its concentration may be 1 nM to 100 UM, 10 nM to 100 μM, or 100 nM to 10 μM, and for example about 1 μM.

In step (4), the concentration of the TGFβ signal inhibitor can be appropriately selected by those skilled in the art, depending on the TGFβ signal inhibitor to be used. When the TGFβ signal inhibitor is A83-01, its concentration may be 1 nM to 100 μM, 10 nM to 100 μM, or 100 nM to 10 μM, and for example about 1 μM.

In step (4), the culture period is 5 to 40 days, 7 to 30 days, 10 to 20 days, and for example about 14 days.

The culture temperature is, but not limited to, about 30 to about 40° C., for example about 37° C. The culture may be performed in $CO_2$-containing air atmosphere. The $CO_2$ concentration is, for example, about 2 to about 5%.

Method for Producing a Collecting Duct Progenitor Cell from a Ureteric Bud Tip Cell In one aspect of the present application, provided is a method for producing a collecting duct progenitor cell, comprising:

isolating a ureteric bud tip cell by the method of the present application, and the step of (2') culturing the ureteric bud tip cell in a medium comprising a Wnt signal inhibitor.

"Collecting duct progenitor cell" means a cell that expresses Aquaporin 2 (AQP2), which is a collecting duct principal cell marker, but not Carbonic anhydrase (CA) II, which is an intercalated cell marker. A collecting duct progenitor cell can be confirmed by the expression of AQP2. Optionally, no expression of CAII may be confirmed.

In step (2'), the ureteric bud tip cell is cultured in a medium comprising a Wnt signal inhibitor. In one embodiment, in step (2'), the ureteric bud tip cell is cultured under an adherent culture condition. In the present application, "adherent culture" refers to cell culture in the manner that the cells are adhered to a culture substrate, e.g., the cells are cultured in a culture plate with coating treatment. Examples of coating materials include laminin, such as laminin-511, laminin-111, and laminin-411, Matrigel (BD), Synthemax (Corning), collagen, gelatins, heparan sulfate proteoglycan, entactin, and fragments and combinations thereof. In the present application, the single cells may be cultured on a cell culture plate coated with extracellular matrix proteins, such as laminin. Commercially available coating materials, such as iMatrix-511 silk, may be used.

In step (2'), the concentration of the Wnt signal inhibitor can be appropriately selected by those skilled in the art, depending on the Wnt signal inhibitor to be used. When the Wnt signal inhibitor is IWR-1, its concentration may be 1 nM to 100 μM, 10 nM to 100 μM, or 100 nM to 10 μM, and for example about 1 μM.

In step (2'), the medium may further comprise a TGEβ signal inhibitor. The concentration of the TGFβ signal inhibitor can be appropriately selected by those skilled in the art, depending on the TGFβ signal inhibitor to be used. When the TGFβ signal inhibitor is A83-01, its concentration may be 1 nM to 100 μM, 10 nM to 100 μM, or 100 nM to 10 μM, and for example about 1 μM.

In step (2'), the culture period may be 2 to 21 days, 3 to 14 days, or 5 to 10 days, and for example about 7 days.

The culture temperature is, but not limited to, about 30 to about 40° C., for example about 37° C. The culture may be performed in $CO_2$-containing air atmosphere. The $CO_2$ concentration is, for example, about 2 to about 5%.

Method for Producing a Collecting Duct Progenitor Cell from a Ureteric Bud Tip Cell Colony In one aspect of the present application, provided is a method for producing a collecting duct progenitor cell, comprising:

obtaining a ureteric bud tip cell colony by the method of the present application, and the steps of (3'-1) dissociating the ureteric bud tip cell colony, and (3'-2) culturing the dissociated cell population in a medium comprising a Wnt signal inhibitor.

In step (3'-1), the ureteric bud tip cell colony is dissociated. As a means for dissociating a cell colony, a conventionally known means for dissociating a cell aggregate may be appropriately used. Examples of the means include a means for mechanically dissociating cells, and a means for dissociating cells using dissociation solution having protease activity and collagenase activity, such as Accutase and Accumax, or having only collagenase activity. For example, the means to be used may be the means for dissociating cell aggregates using dissociation solution having protease activity and collagenase activity, such as Accutase, and mechanically and finely dispersing them into single cells.

The step (3'-2) may be performed in the same manner as the step (2') in the above method for producing a collecting duct progenitor cell from a ureteric bud tip cell.

Method for Monitoring a Ureteric Bud Tip Cell

In one aspect of the present application, provided is a method for monitoring a ureteric bud tip cell, comprising the following steps of:

(i) contacting a biological tissue, a tissue fragment, cultured cells, or a cultured tissue predicted to comprise the ureteric bud tip cell with a VLDL-R binding agent, and (ii) detecting the binding agent. Examples of VLDL-R binding agents used in this aspect are as described above. In a preferred embodiment, the VLDL-R binding agent is labeled as described above. In a more preferred embodiment, the VLDL-R binding agent is labeled VLDL.

The biological tissue, tissue fragment, cultured cells, or cultured tissue predicted to comprise the ureteric bud tip cell can be of mammalian origin. Examples of the mammals include humans and non-human animals, such as mice, rats, hamsters, guinea pigs, cattle, horses, pigs, sheep, monkeys, orangutans, chimpanzees, dogs, cats, and birds. For example, the biological tissue, tissue fragment, cultured cells, or cultured tissue predicted to comprise the ureteric bud tip cell can be of mouse or human origin.

In step (i), the VLDL-R binding agent is typically added to a culture medium of the biological tissue, tissue fragment, cultured cells, or cultured tissue predicted to comprise the ureteric bud tip cell.

In step (ii), as the means for detecting the binding agent, a known means may be appropriately used depending on the type of the binding agent. For example, the binding agent may be labeled as described above, and the label may be used as an indicator. Alternatively, a labeled antibody that recognizes the binding agent may be added, and the label may be used as an indicator. As the means for detecting the binding agent using the label as an indicator, a known method may be appropriately used depending on the type of the label. For example, when the label is a fluorescent label, the fluorescence caused by the label can be detected using a fluorescence microscope.

Composition for Isolating or Monitoring a Ureteric Bud Tip Cell

In one aspect of the present application, provided is a composition for isolating or monitoring a ureteric bud tip cell, comprising a VLDL-R binding agent. Examples of VLDL-R binding agents used in this aspect are as described above.

The composition of the present application can be produced as liquid formulation by adding distilled water, a pH regulator, a suspending agent, a solubilizing agent, a stabilizing agent, an isotonic agent, an antioxidant, a preservative, and the like to a VLDL-R binding agent as appropriate. Examples of pH regulators include hydrochloric acid, sodium hydroxide, lactose, lactic acid, sodium, dibasic sodium phosphate, and monobasic sodium phosphate. Examples of suspending agents include methylcellulose, polysorbate 80, hydroxyethyl cellulose, gum arabic, powdered tragacanth, carboxymethyl cellulose sodium, and polyoxyethylene sorbitan monolaurate. Examples of solubilizing agents include polyoxyethylene hydrogenated castor oil, polysorbate 80, nicotinic-acid amide, and polyoxyethylene sorbitan monolaurate. Examples of stabilizing agents include sodium sulfite, sodium metasulfite, and ether. Examples of isotonic agents include sodium chloride and dextrose. Examples of preservatives include methyl-p-oxybenzoate, ethyl-p-oxybenzoate, sorbic acid, phenol, cresol, and chlorocresol.

EXAMPLE

This invention is described in more detail referring to following examples. This invention, however, is not limited by those Examples in any way.

FIG. 1 shows a schematic diagram summarizing the methods established in the Examples.

Materials and Methods

Cell Culture

The experiments with human induced pluripotent stem cells (hiPSCs) were approved by the Ethics Committee of the Department of Medicine and Graduate School of Medicine, Kyoto University. Three hiPSC lines, 585A1, 1231A3 and 1383D2, were maintained with feeder-free cultures using Stem Fit AK02N medium (Ajinomoto) on cell culture plates coated with 0.25 µL/cm² iMatrix-511 silk (Nippi). The cells were passaged using 0.5 mM EDTA/PBS (Thermo Fisher Scientific) every four days. The cells were routinely monitored for *mycoplasma* contamination.

Differentiation

The cells were directed into ureteric bud (UB) lineages as described previously with some modifications (Mae, SI. & Ryosaka, M. et al. Biochem Biophys Res Commun. 495, 954-61 (2018)). Details of the growth factors and the small molecules used in the Examples are shown in Table 1.

TABLE 1

| Name | Company | Catalog Number |
| --- | --- | --- |
| A83-01 | WAKO | 035-24113 |
| Activin A | R&D | 338-AC |
| BMP4 | Peprotech | AF-120-05ET |
| CHIR99021 | Stem RD | CHIR-010 |
| EGF | R&D | 236-EG-01M |
| FGF1 | R&D | 231-BC |
| FGF8 | Peprotech | 100-25 |
| FGF9 | Peprotech | 100-23 |
| GDNF | R&D | 212-GD |
| IWR-1 | MERCK | I0161-5MG |
| LDN193189 | Axon Medchem | AxonI509 |
| TTNPB | Santa Cruz Biotechnology | sc-203303 |
| Thiazovivin | Santa Cruz Biotechnology | SCB-SC-361380-10 |

Anterior Intermediate Mesoderm Induction hiPSCs were plated at a density of $5 \times 10^4$ cells/well in 4-well culture plates (Thermo Fisher Scientific) in Stem Fit AK02N medium with 10 UM Y-27632 (WAKO) and 0.25 µL/cm² iMatrix-511 silk. After 24 h, the cells were washed with PBS and treated with Essential 6 medium (Thermo Fisher Scientific) containing 100 ng/ml Activin A (R&D Systems) and 3 µM CHIR99021 (Stem RD). After 24 h, the cells were washed with PBS and treated with Essential 6 medium containing 0.1 µM LDN193189 (Axon Medchem), 1 µM A83-01 (WAKO), 0.1 µM 4-[(E)-2-(5, 6, 7, 8-Tetrahydro-5, 5, 8, 8-tetramethyl-2-naphthalenyl)-1-propenyl]-benzoic acid (TTNPB; Santa Cruz Biotechnology) and 200 ng/ml fibroblast growth factor (FGF) 8 (Peprotech) for 2 days. Then, the cells were replated at a density of $2 \times 10^5$ cells/well in Matrigel or Geltrex (Corning) coated 24-well culture plates in Essential 6 medium containing the same 4 factors and 10 µM Y-27632 and incubated for an additional 24 h to induce anterior intermediate mesoderm (AIM).

Nephric Duct (ND) Induction

AIM cells were treated with Essential 6 medium containing 1 µM CHIR99021, 0.1 µM LDN193189, 200 ng/ml FGF8, 100 ng/ml glial cell line-derived neurotrophic factor (GDNF; R&D Systems) and 0.1 µM TTNPB for 2 days to induce ND leading edge cells (ND leader cells). To enhance epithelialization in 2D cultures, AIM cells were treated with the same medium and inducing factors for 8 days. ND leader cells were dissociated into single cells by pipetting after treatment with Accutase (Innovative Cell Technologies) for 3 min at 37° C. The cells were seeded onto low-attachment 96-well plates (Sumitomo Bakelite) at a density of $1 \times 10^4$ cells/well and treated with the same medium and factors with 10 µM Y-27632 to induce mature ND aggregates for 2 days.

Induced Ureteric Bud (iUB) Organoid Induction

Unwanted cells were removed from the ND aggregates by pipetting (Mae, SI. & Ryosaka, M. et al. Biochem Biophys Res Commun. 495, 954-61 (2018)). The ND aggregates were treated with the same medium and factors containing 2% Matrigel for 6 days to constitute iUB organoids with epithelial polarity and tubular lumens. 50 ng/ml EGF (R&D Systems) and 200 ng/ml FGF1 (R&D Systems) were added to enhance budding. The tips were mechanically separated from iUB organoids and cultured in the same medium and factors containing 2% Matrigel for 6 to 14 days to reconstitute branching iUB organoids. The tips separated from the reconstituted iUB organoids were treated with the same medium and factors to repeatedly reconstitute iUB organoids.

Collecting Duct Progenitor Induction

For 2D cultures, day 7 tip cell colonies detached from hydrogel were dissociated into single cells by pipetting after treatment with Accutase for 3 min at 37° C. The single cells were resuspended with Essential 6 medium containing 1 µM IWR-1 (Tocris) and 0.5 µL/cm² iMatrix-511 silk with or without 1 µM A83-01 and seeded at a density of $4 \times 10^4$ cells/well in 96-well plates. For 3D cultures, day 14 reconstituted iUB organoids were treated with Essential 6 medium containing 1 µM IWR-1 and 1 µM A83-01 for 14 days.

ND Cryopreservation

The dissociated ND leader cells were resuspended with STEM-CELLBANKER GMP grade (Nippon Zenyaku Kogyo Co., Ltd.) at a dilution ratio less than $1 \times 10^6$ cells/mL. The cell suspension was dispensed to each cryopreservation tube. The tubes were frozen at −80° C. for 24 h and then, placed in a liquid nitrogen cell tank storage for long-term cryopreservation. To initiate cultures, the cells were thawed using a water bath at 37° C. Then, the cells were slowly resuspended with Essential 6 medium containing 10 µM Y-27632 and centrifuged at 200 g for 5 min at room temperature. After removal of the supernatant, the cells were resuspended with Essential 6 medium containing ND induction factors with 10 µM Y-27632 and seeded onto low-attachment 96-well plates at a density of $1 \times 10^4$ cells/well.

Tip Cell Expansion

The iUB organoids were treated with Accutase for 5 min at 37° C. and subsequently dissociated into single cells by pipetting. The cells were resuspended with DMEM/F12 medium (Thermo Fisher Scientific) containing B-27 Supplement, minus vitamin A (Thermo Fisher Scientific), 100 ng/ml GDNF, 200 ng/ml FGF1, 0.1 µM TTNPB, 3 µM CHIR99021 and 10 UM Thiazovivin (Santa Cruz Biotechnology). The single cells obtained from 10 iUB organoids were seeded onto one well of 48-well plates coated with 150 µL hydrogel, which is composed of DMEM/F12 medium containing 50% Matrigel and was solidified for 30 min at 37° C. before use. The single cells constructed tip cell colonies after 6-7 days. The medium was refreshed every 2 days.

Reconstitution of iUB Organoids from Single Tip Cells

Hydrogel was dissolved with Cell Recovery Solution (BD Biosciences) for 1 h at 4° C. to detach day 7 tip cell colonies. After washing with additional Cell Recovery Solution, the tip cell colonies were centrifuged at 500 g for 5 min at room temperature. Essential 6 medium containing 0.1 µM LDN193189, 100 ng/ml GDNF, 0.1 µM TTNPB, 200 ng/ml FGF8, 1 µM CHIR99021 or 10% Afamin/Wnt3a conditioned medium (MBL), 200 ng/ml R-spondin 1 (R&D systems), 50 ng/ml EGF, 200 ng/ml FGF1 and 10% Matrigel was applied to the tube including tip cell colonies. After pipetting gently with a wide-mouth micropipette (BMBio) not to break colonies, the suspension was distributed to low-attachment 35 mm dish (Sumitomo Bakelite) at 2 mL/dish. The medium was refreshed every 2 days. On day 4, each colony was placed onto one well of low-attachment 96-well plates in the same medium. After an additional 6 days, the tip region was separated from the reconstituted iUB organoid and treated with the same medium for 35 days.

Maintenance Culture of the Tip Cell Colonies

The iUB organoids were treated with Accutase for 5 min at 37° C. and subsequently dissociated into single cells by pipetting. The cells were suspended with DMEM/F12 medium containing B-27 Supplement, minus vitamin A, 100 ng/ml GDNF, 200 ng/ml FGF1, 0.1 µM TTNPB, 3 µM CHIR99021, 10 µM Thiazovivin, and 1 µM A83-01. The cells were seeded onto one well of 48-well plates coated with 150 µL hydrogel, which is composed of DMEM/F12 medium containing 50% Matrigel and was solidified for 1 h at 37° C. before use. The single cells were cultured at 37° C. and 5% $CO_2$ for 7 days to construct tip cell colonies. The medium was refreshed every 2 to 3 days. The constructed tip cell colonies were passaged in the same medium every 7 days. The iUB organoids were reconstituted from the tip cell colonies constructed or passaged for three times using the same method as above.

Monitoring of the Tip Cells Using DiI-Conjugated VLDL (DiI-VLDL)

The iUB organoids, tip cell colonies and ND aggregates were treated with 10 µg/ml DiI-conjugated VLDL (Biomedical Technologies, Inc.) for 2 h at 37° C.

Flow Cytometry Analysis

The iUB organoids and tip cell colonies treated with DiI-VLDL were dissociated into single cells by pipetting after Accutase treatment for 3 min at 37° C. After washing with DMEM/10% FBS, the cells were re-suspended with PBS/2% FBS. The single cells were analyzed and sorted using FACS Aria II (BD). Cells derived from iUB organoids and tip cell colonies without DiI-VLDL treatment were used as negative controls for gating.

RNA Sequencing Analysis

The day 6 iUB organoids were treated with DiI-VLDL for 2 h. Flow cytometry analysis was performed to sort DiI-VLDL$^+$ and DiI-VLDL$^-$ cells. Total RNA of sorted DiI-VLDL$^+$ and DiI-VLDL$^-$ cells was isolated using Nucleo-Spin RNA XS (Takara). The samples were preserved at −80° C. and RNA sequencing analysis was performed by DNAFORM Co., Ltd.

Immunostaining

Immunostaining analysis was performed as described previously with some modifications (Mae, SI. & Ryosaka, M. et al. Biochem Biophys Res Commun. 495, 954-61 (2018)). For 2D cultures, the cells were fixed with 4% paraformaldehyde (PFA)/PBS for 20 min at 4° C. After washing with PBS twice, the cells were blocked with 18 normal donkey serum (MERCK) and 3% bovine serum albumin (BSA; Nacalai Tesque)/PBST (PBS/0.25% Triton X-100, Nacalai Tesque) for 1 h at room temperature. Primary antibodies were diluted with blocking solution at 1:500 and incubated with the samples overnight at 4° C. After washing with PBST twice, secondary antibodies diluted with blocking solution at 1:500 were incubated for 1 h at room temperature.

For immunostaining analysis of frozen sections, samples were fixed with 4% PFA/PBS for 1 h at 4° C. Fixed samples were treated with 30% sucrose/PBS and frozen with OCT compound (Tissue-Tek) to make frozen sections by cryosectioning. The frozen sections were washed with distilled water and incubated with blocking solution for 1 h at room temperature. Primary antibodies diluted with blocking solution at 1:500 were incubated with the samples overnight at room temperature. After washing with distilled water twice, the cells were incubated with secondary antibodies diluted with blocking solution at 1:500 for 1 h at room temperature.

For 3D imaging analysis, we applied Clear, Unobstructed Brain/Body Imaging Cocktails and Computational analysis (CUBIC) (Susaki EA. et al. Nat protoc. 10, 1709-27 (2015); Nojima S. et al. Sci Rep. 24, 9269 (2017)). After fixation with 4% PFA/PBS for 24 h at 4° C., samples were treated with CUBIC1 solution diluted with distilled water at 1:2 on a seesaw shaker set at 30 rpm for 8 h at room temperature for tissue clearing. Then, the samples were treated with CUBIC1 solution on the seesaw shaker set at 30 rpm for 24 h at room temperature. After washing with PBS, the samples were incubated with blocking solution on the seesaw shaker set at 30 rpm for 2 h at 4° C. Primary antibodies were diluted with blocking solution and incubated with the samples on a seesaw shaker set at 30 rpm for 24 h at 4° C. After washing with blocking solution, the cells were incubated with secondary antibodies on a seesaw shaker set at 30 rpm for 24 h at 4° C. After washing with PBS twice, the samples were treated with CUBIC2 solution diluted with PBS at 1:2 on a seesaw shaker set at 30 rpm for 8 h at room temperature. Then, the samples were treated with CUBIC2 solution on a seesaw shaker set at 30 rpm for 24 h at room temperature. Then, the samples were analyzed with Zeiss LSM710 (Zeiss). Details of the primary antibodies used in the Examples are shown in Table 2.

TABLE 2

| Antigen | Host Species | Company | Catalog Number |
|---|---|---|---|
| AQP2 | mouse | Santa Cruz Biotechnology | sc-515770 |
| CAII | rabbit | Abcam | AB124687-100 |
| CK8 | mouse | Abcam | ab9023 |

TABLE 2-continued

| Antigen | Host Species | Company | Catalog Number |
|---|---|---|---|
| E-CADHERIN | mouse | BD | 610181 |
| E-CADHERIN | goat | R&D | AF648 |
| EZRIN | mouse | Abcam | Ab4069 |
| FOXA1 | mouse | Santa Cruz Biotechnology | sc-514695 |
| GATA3 | rabbit | Cell signaling | 5852S |
| GATA3 | goat | R&D | AF2605 |
| LAMININ | rabbit | MERCK | L9393-2ML |
| PAX2 | rabbit | BioLegend | PRB-276P |
| PAX2 | goat | R&D | AF3364 |
| RET | goat | R&D | AF1485 |
| VLDLR | mouse | Santa Cruz Biotechnology | sc-18824 |
| SOX9 | mouse | Abcam | ab76997 |

Details of the secondary antibodies (Thermo Fisher Scientific) used in the Examples are shown in Table 3. In the Examples, the secondary antibodies listed in Table 3 were used in appropriate combinations.

TABLE 3

| Name | Catalog Number |
|---|---|
| Donkey anti-Rabbit IgG (H + L) Highly Cross-Adsorbed Secondary Antibody, Alexa Fluor 488 | A-21206 |
| Donkey anti-Mouse IgG (H + L) Highly Cross-Adsorbed Secondary Antibody, Alexa Fluor 488 | A-21202 |
| Donkey anti-Goat IgG (H + L) Cross-Adsorbed Secondary Antibody, Alexa Fluor 488 | A-11055 |
| Donkey anti-Rabbit IgG (H + L) Highly Cross-Adsorbed Secondary Antibody, Alexa Fluor 546 | A10040 |
| Donkey anti-Mouse IgG (H + L) Highly Cross-Adsorbed Secondary Antibody, Alexa Fluor 546 | A10036 |
| Donkey anti-Goat IgG (H + L) Cross-Adsorbed Secondary Antibody, Alexa Fluor 546 | A-11056 |
| Donkey anti-Rabbitt IgG (H + L) Highly Cross-Adsorbed Secondary Antibody, Alexa Fluor 647 | A-31573 |
| Donkey anti-Mouse IgG (H + L) Highly Cross-Adsorbed Secondary Antibody, Alexa Fluor 647 | A-31571 |
| Donkey anti-Goat IgG (H + L) Cross-Adsorbed Secondary Antibody, Alexa Fluor 647 | A-21447 |

CUBIC1 solution is a mixture of urea (10% final concentration, Nacalai Tesque), Quadrol (25% final concentration, Tokyo Chemical Industry), Triton X-100 (5% final concentration), 5M NaCl and distilled water. CUBIC2 solution is a mixture of urea (25% final concentration), sucrose (50% final concentration, Nacalai Tesque), triethanolamine (10% final concentration, Wako) and distilled water. Hoechst33342 (Thermo Fisher Scientific, Catalog Number: H1399) was used as a nuclear staining agent.

Statistical Analysis

Data of flow cytometry and cell count analyses were presented as mean±SE. Statistical analysis for difference between two groups was performed using Student's t test. Differences were considered significant when p<0.05.

[Results]

The inventors first modified their previously-reported nephric duct (ND) induction method by adding a retinoic acid (RA) agonist, TTNPB, to Stage 4 treatment because RA signals play crucial roles in ND development (Stewart, K. & Bouchard, M. Semin Cell Dev Biol. 36, 13-20 (2014)) (FIGS. 2 and 3). The inventors also found that prolonged treatment with ND elongation factors used at Stage 4 induced epithelialization of ND cells (FIG. 4). Therefore, the inventors generated ND epithelial aggregates with using the same inducing factors as Stage 4 and removed unwanted cells by pipetting (FIG. 5).

Figures 6, 7, 8, 9:
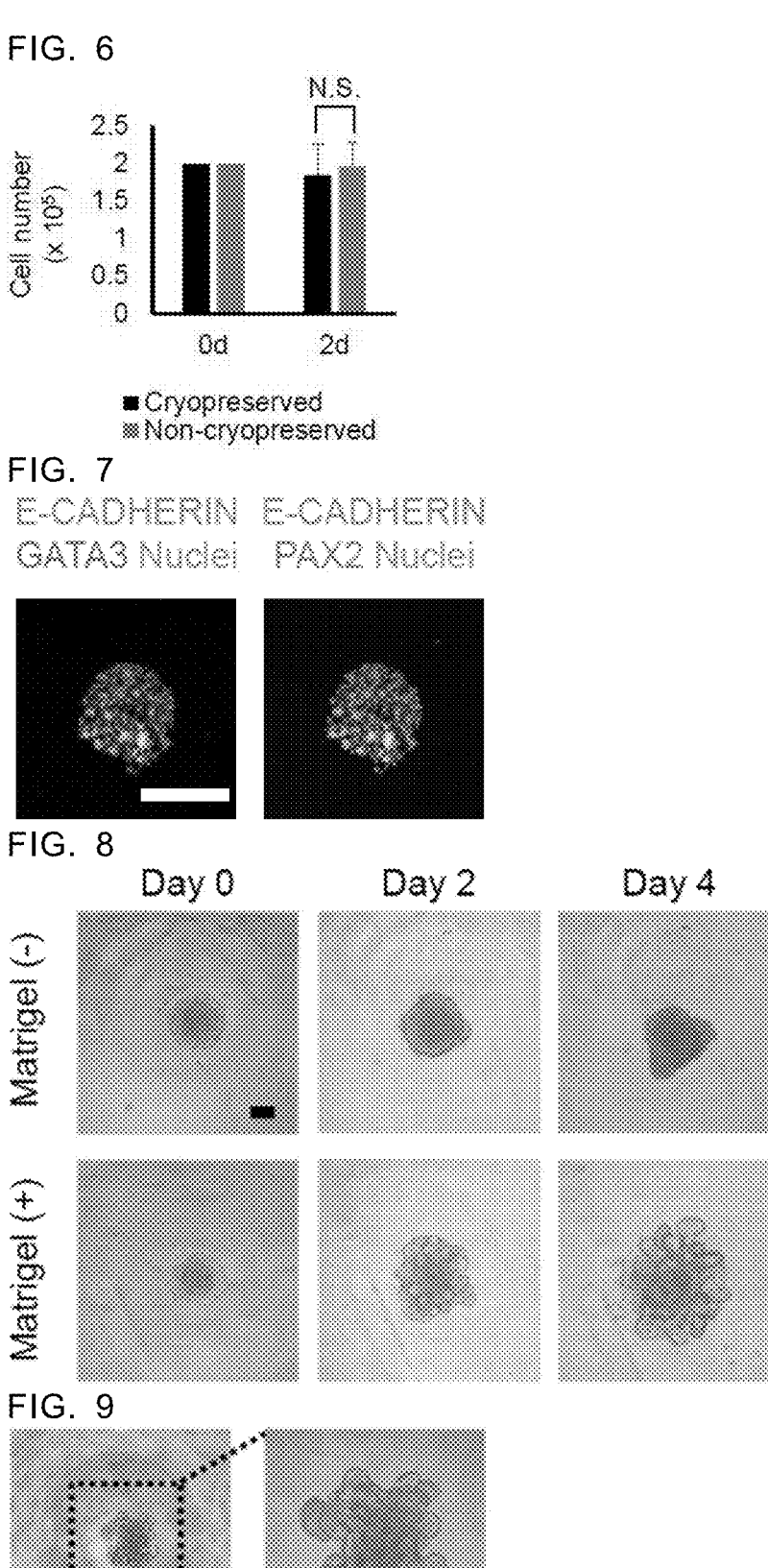
FIG. 6 No significant differences were found in the number of cells on ND maturation stage (Stage 5) day 2 with or without cryopreservation (n=3).
FIG. 7 Immunostaining analysis of Stage 5 day 2 ND aggregate generated from cryopreserved ND leader cells for E-CADHERIN (green), GATA3 (red) and PAX2 (purple). Scale bar: 100 μm.
FIG. 8 Morphological changes of ND aggregates for 4 days with or without low concentration Matrigel. Scale bar: 100 μm.
FIG. 9 Morphology of a day 6 iUB organoid. Right panel is a magnified view of the boxed area in left panel. Scale bars: 300 μm.
Figures 14, 15, 16:
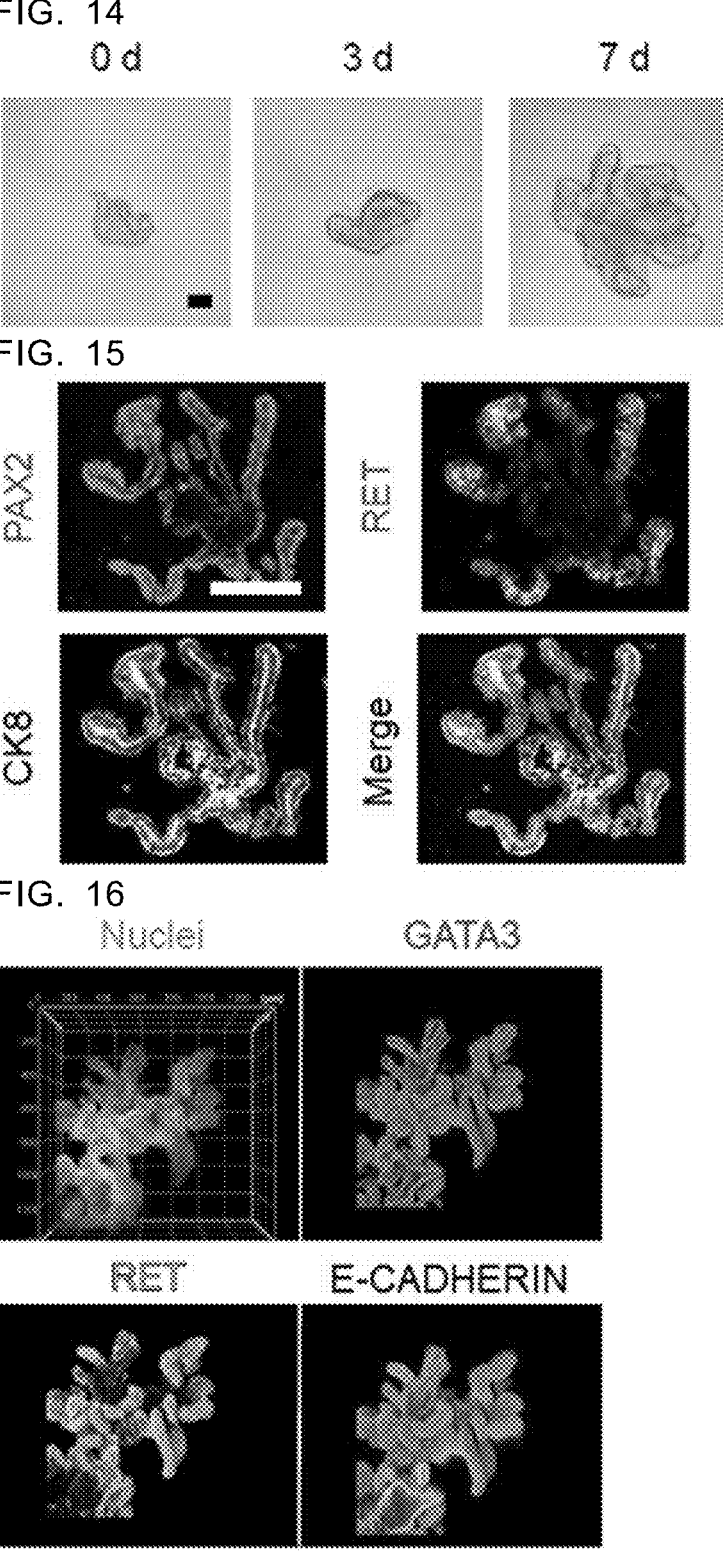

A commercially available cryopreservation reagent is useful for stocking ND leading edge cells (ND leader cells) at Stage 4, because the stocked cells maintain the potential to form ND epithelial aggregates to the same extent as non-cryopreserved ND leader cells (FIGS. 6 and 7).

Figures 10, 11, 12, 13:
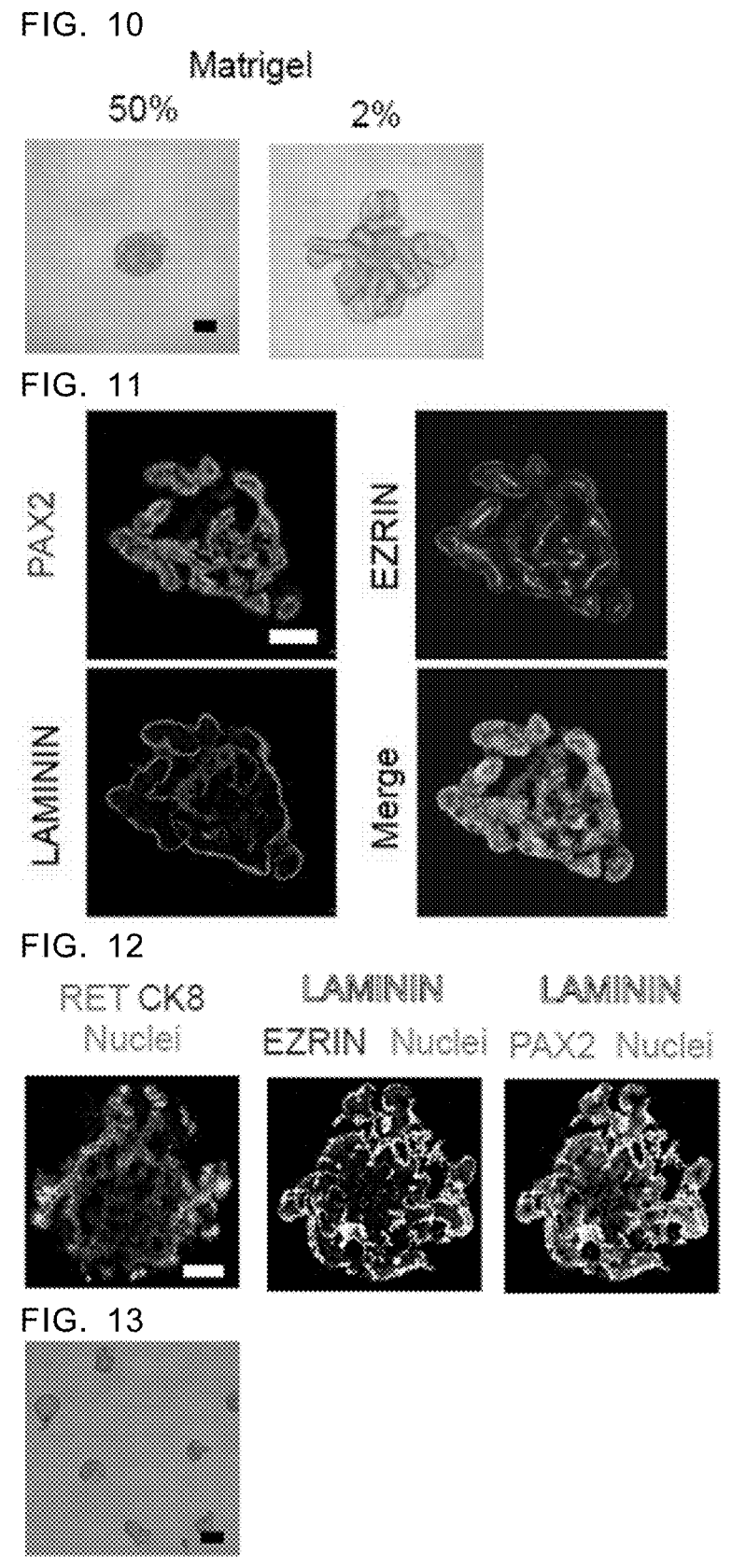

The addition of low concentrations of Matrigel to the culture media was reported to promote the organization of continuous epithelial tissues (Koehler, K. R. et al. Nat Biotechnol. 35, 583-9 (2017)). Accordingly, the inventors added low concentration (2%) of Matrigel to the ND aggregate cultures, which effectively induced UB-like structures (FIGS. 8 to 10). Immunostaining analysis showed that these UB-like structures expressed an apical marker, EZRIN, and a basal marker, LAMININ. This result indicates that these structures have apicobasal polarity and tubular lumens, in addition to the formation of differential domains of RET$^+$ tip and CK8$^+$ trunk, and the structure having these features is referred to as iUB organoid (FIGS. 11 and 12).

Figures 17, 18, 19:
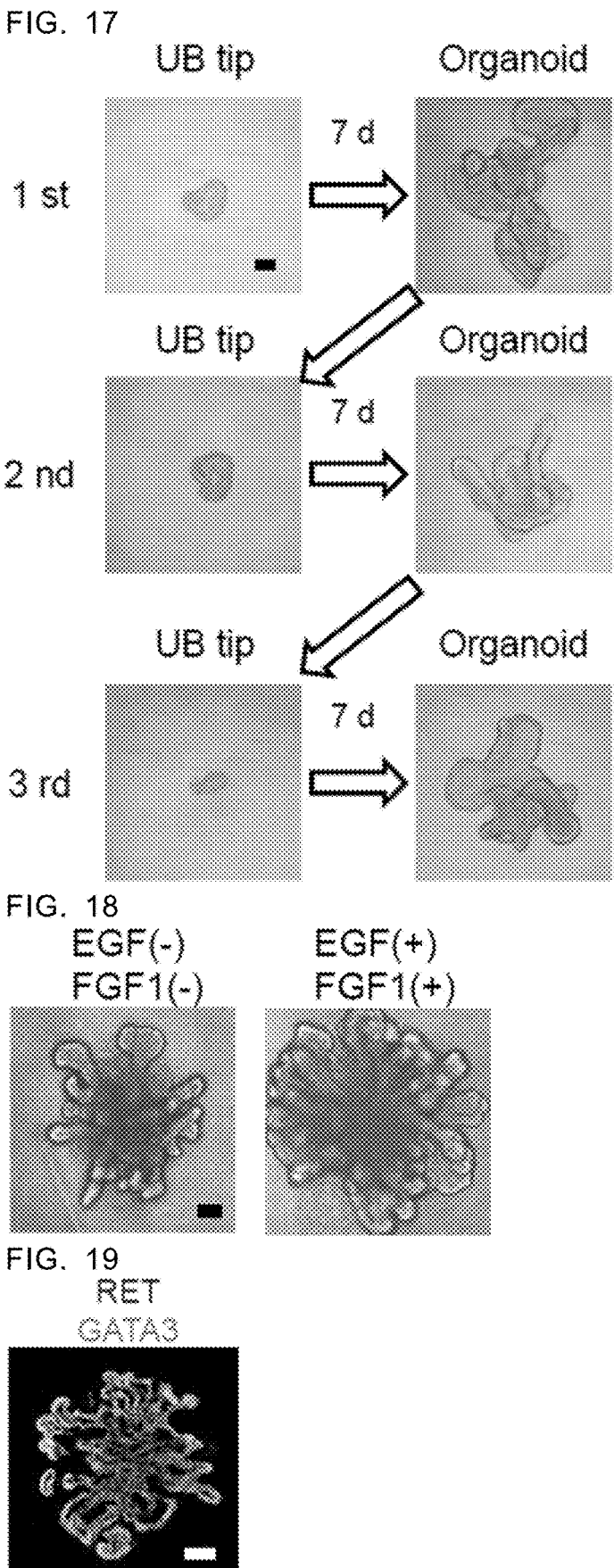
FIG. 17 Morphological changes of a separated tip for 7 days. A tip separated from reconstituted iUB organoid repeats branching morphogenesis and reconstitutes iUB organoid. Scale bar: 100 μm.
FIG. 18 Morphology of iUB organoids cultured in organoid medium without or with EGF and FGF1. Scale bar: 100 μm.
FIG. 19 Immunostaining analysis of a day 6 iUB organoid cultured in organoid medium containing EGF and FGF1 for RET (red) and GATA3 (green). Scale bar: 100 μm.

The inventors then manually separated the tips from iUB organoids and cultured them in the same medium containing low concentration of Matrigel (hereafter called organoid medium; FIG. 13). The separated tips formed branching structures with tip and trunk regions and epithelial polarity similar to the original iUB organoids (FIGS. 13 to 16), suggesting the reconstitution of iUB organoids. Moreover, the tips separated from the reconstituted iUB organoids again reconstituted iUB organoids with branching morphogenesis. This reconstitution process can be repeated at least three times, finding that total branching number was approximately 20 times (FIG. 17). Furthermore, the inventors found that adding EGF and FGF1 to organoid medium promoted budding which had tip and trunk structures and epithelial polarity (FIGS. 18 to 20).

Figures 25, 26:
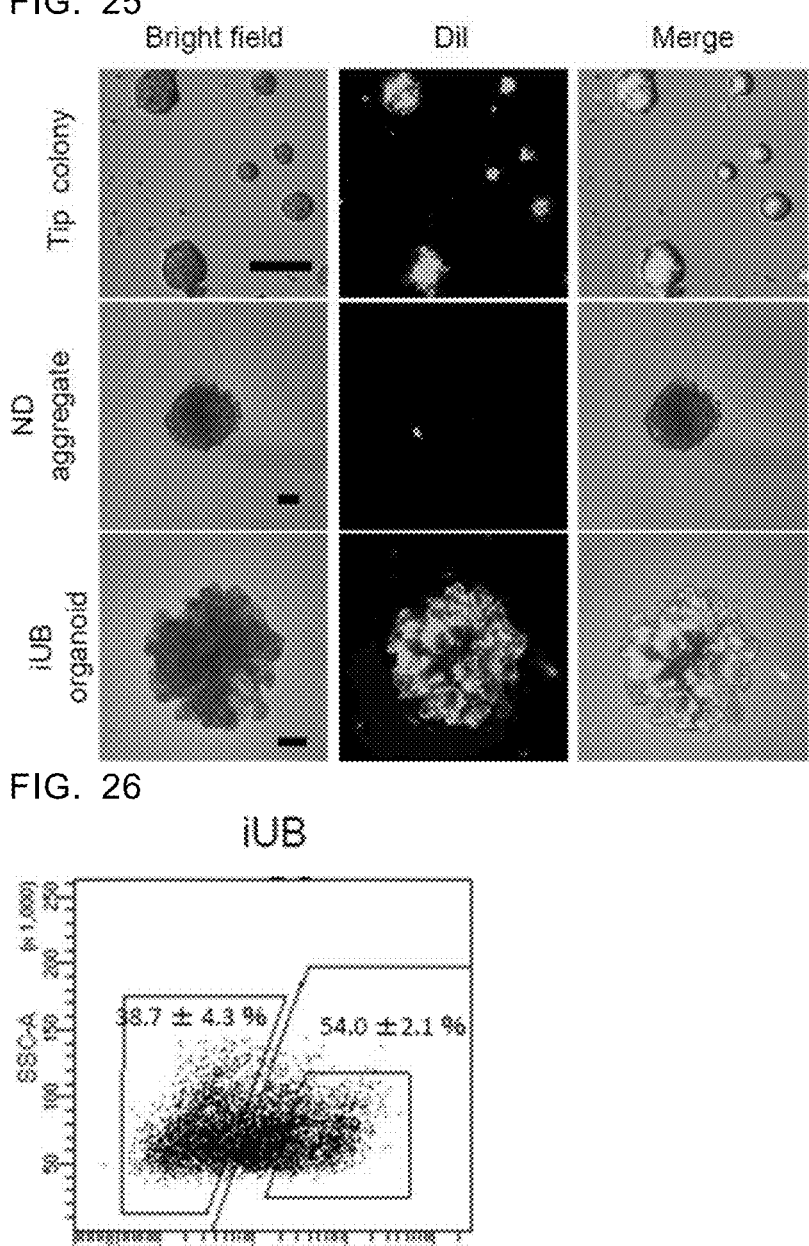
FIG. 25 Images of tip cell colonies, a ND aggregate and an iUB organoid for bright field and fluorescence microscopy analysis after DiI-conjugated VLDL (DiI-VLDL) uptake. Scale bars: 100 μm.
FIG. 26 Results of FACS analysis of iUB organoids for DiI-VLDL expression.
Figure 27:
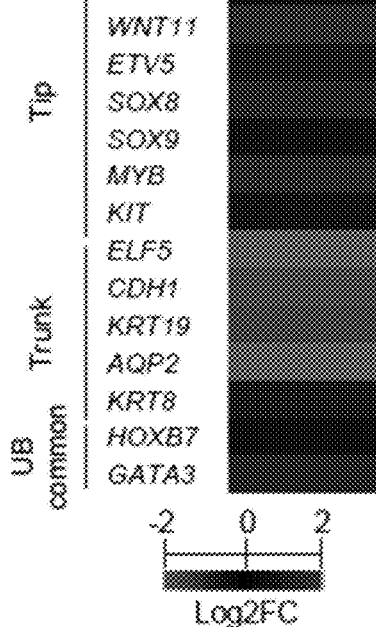
FIG. 27 Heatmap showing differentially expressed genes between DiI-VLDL$^+$ and DiI-VLDL$^-$ cells determined by RNA sequencing analysis. indicates The heatmap that the expression of genes associated with tips (Tip) was increased in DiI-VLDL$^+$ cells, and the expression of genes associated with trunks (Trunk) was higher in DiI-VLDL$^-$ cells.
Figure 28:
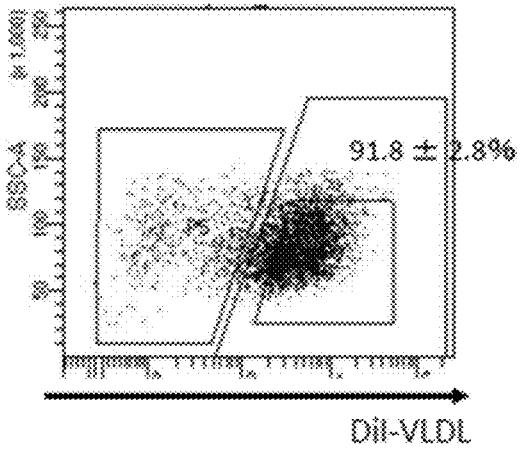
FIG. 28 Results of FACS analysis of tip cell colonies for DiI-VLDL expression.
Figure 29:
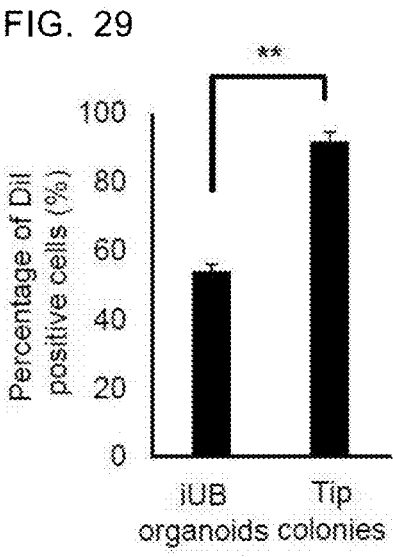
FIG. 29 The ratio of DiI-VLDL+ cells in iUB organoids and tip cell colonies. *p<0.05 and **p<0.001 by Student's t test.
Figure 30:
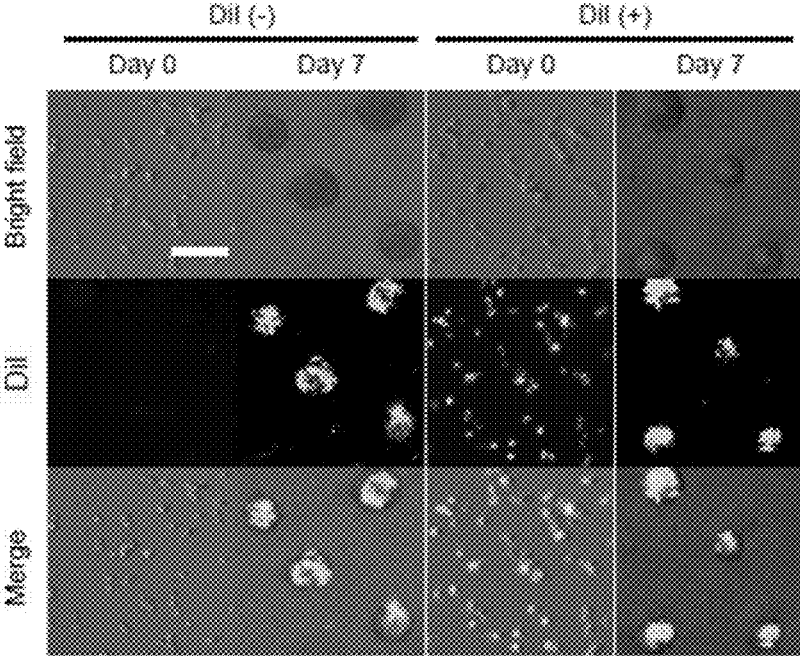
FIG. 30 Fluorescence microscopy analysis of DiI-VLDL$^-$ and DiI-VLDL$^+$ cells on days 0 and 7. Note that the tip cell colonies importing DiI-VLDL are derived from not only DiI$^+$ cells, but also DiI-cells. Scale bar: 100 μm.
Figure 31:
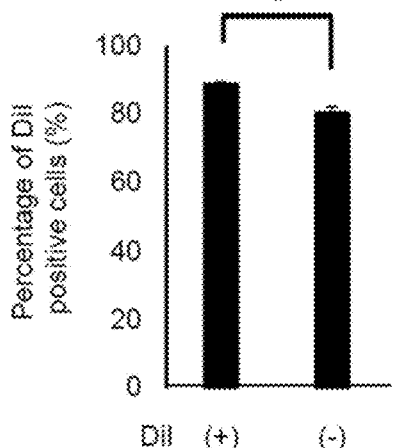
FIG. 31 The ratio of DiI-VLDL⁺ cells in day 6 tip cell colonies derived from single DiI-VLDL⁺ and DiI-VLDL-cells. *p<0.05 and **p<0.001 by Student's t test.

The inventors next aimed to obtain a large amount of iUB organoids. The inventors found that single cells from iUB organoids seeded on a soft hydrogel successfully expanded to form colonies that resembled UB tips expressing RET and GATA3 (FIGS. 21 to 23). Then, in order to reveal the origin of tip cell colonies, the inventors tried to develop methods to monitor tip cell development. Consistent with previous reports, the inventors found that very low density lipoprotein (VLDL) receptor is expressed in tip regions by immunostaining analysis (FIG. 24) (Yuri, S. et al. Stem Cell Reports. 8, 401-16 (2017); Rutledge, E. A., Benazet, J. D. & McMahon, A. P. Development. 144, 3177-88 (2017)). Therefore, the inventors hypothesized that tip cells might specifically import VLDL and examined the uptake of VLDL conjugated with DiI (DiI-VLDL) by tip cell colonies, ND epithelial aggregates and iUB organoids. As expected, whole tip cell colonies and tip regions of iUB organoids, but not ND aggregates, imported DiI-VLDL (FIG. 25). Additionally, RNA sequencing analysis comparing DiI$^+$ and DiI$^-$ cells purified by flow cytometry indicated the upregulated expression of tip-related genes in DiI$^+$ cells, while the expression of trunk-related genes was higher in DiI$^-$ cells (FIGS. 26 and 27). This tip-monitoring technique with DiI$^-$ VLDL showed that the ratio of tip cells increased from 54.0±2.1% to 91.8±2.8% with the inventors' hydrogel culture (n=3, FIGS. 26, 28, and 29). Next, the inventors cultured isolated single DiI$^+$ and DiI$^-$ cells on hydrogel. Interestingly, tip cell colonies importing DiI-VLDL were derived from not only DiI$^+$ cells, but also DiI$^-$ cells after 7 days (FIG. 30). The ratio of tip cells derived from DiI$^-$ cells was high at 80.5±1.6%, although significantly lower than that from DiI$^+$ cells (88.9±0.5%, FIG. 31). These results are consistent with the previous findings that UB trunk cells can regenerate tip cells in vitro (Yuri, S. et al. Stem Cell Reports. 8, 401-16 (2017)).

Then, the inventors cultured tip cell colonies in organoid medium, which resulted in the reconstitution of branching iUB organoids with tip and trunk regions and epithelial polarity (FIGS. 32 and 33). Moreover, the inventors found that tips separated from expanded iUB organoids showed branching morphogenesis, demonstrating the establishment of a simplified expansion method of tip cells with the developmental potential to give rise to iUB organoids (FIG. 34). However, this reconstitution process of iUB organoids was only observed with tip cell colonies derived from 585A1 iPS cells. In order to establish the robust reconstitution method of iUB organoids from tip cell colonies, the inventors focused on the Wnt signaling pathway. The inventors replaced CHIR99021 with Wnt3a conditioned medium and R-spondin 1 in organoid medium. Consequently, the inventors found that iUB organoids could be reconstituted from tip cell colonies derived from any iPS cell lines (FIG. 35).

Figures 36, 37, 38, 39:
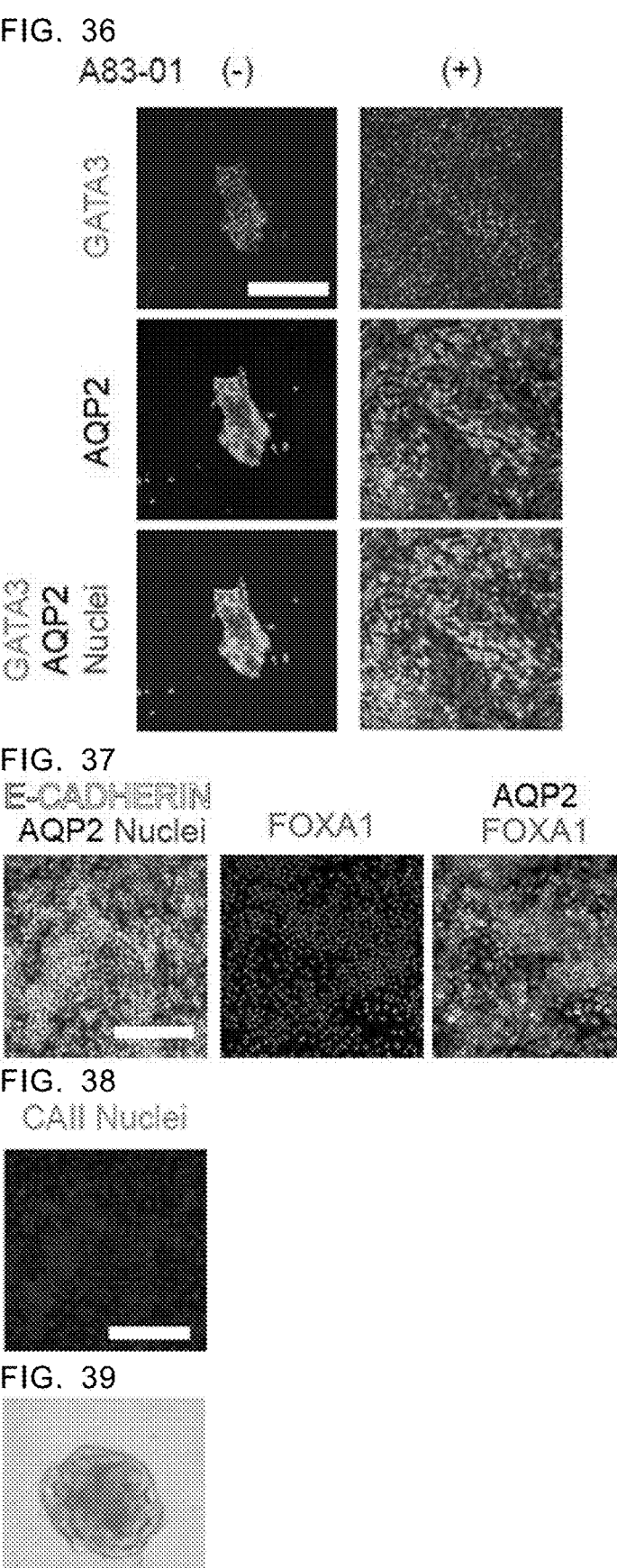
FIG. 36 Immunostaining analysis of dissociated tip cells on day 7 of 2D culture in the medium with or without A83-01 for GATA3 (green) and AQP2 (red). Scale bar: 100 µm.
FIG. 37 Immunostaining analysis of dissociated tip cells on day 7 of 2D culture for AQP2 (red), E-CADHERIN (white), and FOXA1 (green). Scale bar: 100 µm.
FIG. 38 Immunostaining analysis of dissociated tip cells on day 7 of 2D culture for an intercalated cell marker, CAII (green). Scale bar: 100 µm.
FIG. 39 Morphology of a day 14 collecting duct progenitor organoid. Scale bar: 100 µm.

Next, because Wnt/β-catenin signals maintain stem cells in UB tip regions (Rutledge, E. A., Benazet, J. D. & McMahon, A. P. Development. 144, 3177-88 (2017)), the inventors retrieved tip cell colonies from the hydrogel and cultured them using a WNT signal inhibitor, IWR-1, to differentiate trunk cells. The inventors found that the treatment with IWR-1 facilitated the differentiation of dissociated tip colony cells into the cells expressing a collecting duct principal cell marker, Aquaporin (AQP) 2, but not an intercalated cell marker, Carbonic anhydrase (CA) II, and the combination of IWR-1 and a TGFβ signal inhibitor, A83-01, improved the induction rates of these cells (FIGS. 36 to 38). Moreover, the inventors succeeded in inducing reconstituted iUB organoids derived from tip cell colonies into AQP2$^+$ collecting duct progenitor organoids by the same treatment with the same factors (FIGS. 39 and 40). These collecting duct progenitors may resembles collecting ducts of around gestational week (GW) 7 embryos, which express only principal cell markers (Wang, P. et al. Cell Rep. 24, 3554-67 e3 (2018)).

Figure 49:
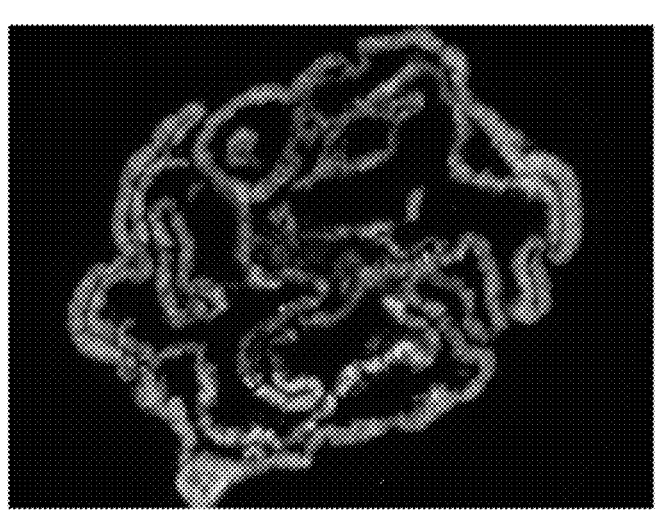
FIG. 49 Immunostaining analysis of an iUB organoid derived from a tip cell colony after three passage cultures for GATA3 (green) and RET (red).

The iUB organoids were dissociated into single cells by Accutase treatment. The single cells were cultured on hydrogels in the medium further containing A83-01, resulting in the production of GATA3$^+$, RET$^+$, SOX9$^+$ ureteric bud tip cell colonies (FIGS. 42 and 43). The produced ureteric bud tip cell colonies were cultured in organoid medium to produce iUB organoids (FIG. 44). The iUB organoids had GATA3$^+$, RET$^+$ tip regions and GATA3$^+$ trunk regions (FIG. 45). The produced ureteric bud tip cell colonies were passaged three times in the same medium (FIGS. 46 and 47). After three passages, the ureteric bud tip cell colonies were cultured in organoid medium, resulting in the production of iUB organoids (FIG. 48). The iUB organoid had GATA3$^+$, RET$^+$ tip regions and GATA3$^+$ trunk regions (FIG. 49).

What is claimed is:

1. A method for isolating a ureteric bud tip cell from cells, a tissue, or an organoid comprising the ureteric bud tip cell, comprising the following steps of:
   (1-1) contacting the cells, tissue, or organoid comprising the ureteric bud tip cell with a labelled very low density lipoprotein (VLDL), and
   (1-2) isolating the ureteric bud tip cell using the labelled VLDL as an indicator,
   wherein the cells, tissue, or organoid comprising the ureteric bud tip cell is differentiated from a human induced pluripotent stem cell.

2. The method according to claim 1, wherein the cells, tissue, or organoid comprising the ureteric bud tip cell is a ureteric bud-like organoid.

3. A method for producing a ureteric bud tip cell colony, comprising:

isolating a ureteric bud tip cell by the method according to claim 1, and the step of (2) culturing the ureteric bud tip cell in a medium comprising glial cell line-derived neurotrophic factor, a fibroblast growth factor, a retinoic acid receptor agonist, a GSK3β inhibitor, and a Yes-associated protein (YAP) activity inhibitor.

4. The method according to claim 3, wherein in step (2), the medium further comprises a TGFβ signal inhibitor.

5. The method according to claim 3, comprising a step of passaging the obtained ureteric bud tip cell colony after step (2).

6. A method for producing a ureteric bud-like organoid, comprising:

obtaining a ureteric bud tip cell colony by the method according to claim 3, and the step of (3) culturing the ureteric bud tip cell colony in a medium comprising a Wnt signaling activator, a BMP inhibitor, a fibroblast growth factor, a retinoic acid receptor agonist, and glial cell line-derived neurotrophic factor to reconstitute the ureteric bud-like organoid.

7. The method according to claim 6, wherein in step (3), the medium further comprises EGF and FGF1.

8. A method for producing a collecting duct progenitor-like organoid, comprising:

obtaining a ureteric bud-like organoid by the method according to claim 6, and the step of (4) culturing the ureteric bud-like organoid in a medium comprising a Wnt signal inhibitor and a TGFβ signal inhibitor.

* * * * *